(12) United States Patent
Heilbrunn et al.

(10) Patent No.: US 9,804,768 B1
(45) Date of Patent: Oct. 31, 2017

(54) METHOD AND SYSTEM FOR GENERATING AN EXAMINATION REPORT

(71) Applicant: ABCDisability, Inc., Redmond, WA (US)

(72) Inventors: Ken Steven Heilbrunn, Seattle, WA (US); Thomas E Sanko, Redmond, WA (US)

(73) Assignee: ABCDisability, Inc., Redmond, WA (US)

( * ) Notice: Subject to any disclaimer, the term of this patent is extended or adjusted under 35 U.S.C. 154(b) by 3 days.

(21) Appl. No.: 14/750,761

(22) Filed: Jun. 25, 2015

Related U.S. Application Data

(60) Provisional application No. 62/017,144, filed on Jun. 25, 2014.

(51) Int. Cl.
| | |
|---|---|
| *G06F 3/0488* | (2013.01) |
| *G06F 3/041* | (2006.01) |
| *G06F 3/0484* | (2013.01) |
| *G06F 3/0481* | (2013.01) |

(52) U.S. Cl.
CPC ............ *G06F 3/0488* (2013.01); *G06F 3/041* (2013.01); *G06F 3/04817* (2013.01); *G06F 3/04842* (2013.01)

(58) Field of Classification Search
CPC ........................... G06F 3/0488; G06F 3/04817
See application file for complete search history.

(56) References Cited

U.S. PATENT DOCUMENTS

| | | | |
|---|---|---|---|
| 6,581,038 B1 * | 6/2003 | Mahran | G06F 17/30702 128/923 |
| 7,792,778 B2 | 9/2010 | Zhou et al. | |
| 7,899,684 B2 | 3/2011 | Fukatsu et al. | |
| 7,979,383 B2 | 7/2011 | Heilbrunn et al. | |
| 8,369,585 B2 | 2/2013 | Graessner et al. | |
| 8,630,842 B2 | 1/2014 | Sorkey et al. | |
| 8,930,210 B2 | 1/2015 | Oez | |
| 8,935,628 B2 | 1/2015 | Chernilo | |
| 2004/0225530 A1 * | 11/2004 | Bell | G06Q 50/22 705/2 |
| 2004/0247166 A1 | 12/2004 | Giger et al. | |
| 2006/0116557 A1 * | 6/2006 | Moore | A61B 5/0002 600/300 |

(Continued)

*Primary Examiner* — Claire X Pappas
*Assistant Examiner* — Robert Stone
(74) *Attorney, Agent, or Firm* — Brian Roffe

(57) ABSTRACT

Method for conducting an examination of an object including specific tasks using a computer and software that when executed, performs the method. Designated content areas, e.g., icons, representing segments are displayed on a touch screen of the computer. When a content area representing a segment is tapped, content areas representing a respective sub-segment are displayed. When a content area representing a sub-segment is tapped, designated content areas representing a respective task are displayed. When a content area representing a task is tapped, instructions to enable performance of the task by the user is displayed. Data entry relating to performance of the task on the object or a condition, property or characteristic of the object needed to complete the task is then accepted then stored in a memory component. A report is generated from the entered data and includes generating text and/or graphics from completion of performance of each task.

25 Claims, 13 Drawing Sheets

(56) References Cited

U.S. PATENT DOCUMENTS

| | | | |
|---|---|---|---|
| 2007/0265542 A1* | 11/2007 | Bardy | A61B 5/0031 600/529 |
| 2008/0086507 A1* | 4/2008 | Szygenda | G06F 17/3064 |
| 2008/0109258 A1* | 5/2008 | Kirschenbaum | G06Q 50/24 705/3 |
| 2008/0270185 A1* | 10/2008 | Gossler | G06Q 50/22 705/2 |
| 2009/0030945 A1* | 1/2009 | Miller | G06F 17/30554 |
| 2009/0204421 A1 | 8/2009 | Guimaraes | |
| 2010/0135562 A1 | 6/2010 | Greenberg et al. | |
| 2010/0138239 A1* | 6/2010 | Reicher | G06F 17/243 705/3 |
| 2010/0189313 A1 | 7/2010 | Prokoski | |
| 2010/0293164 A1 | 11/2010 | Weese et al. | |
| 2011/0202831 A1* | 8/2011 | Bruckner | G06Q 10/10 715/246 |
| 2011/0255760 A1 | 10/2011 | Mahesh et al. | |
| 2011/0295790 A1 | 12/2011 | Zillner | |
| 2012/0004902 A1* | 1/2012 | Sorkey | G06F 19/322 704/9 |
| 2012/0004932 A1* | 1/2012 | Sorkey | G06Q 10/06 705/3 |
| 2012/0020536 A1 | 1/2012 | Moehrle | |
| 2012/0029943 A1* | 2/2012 | Kurahashi | A61B 6/563 705/3 |
| 2012/0158432 A1* | 6/2012 | Jain | G06Q 10/10 705/3 |
| 2013/0290019 A1* | 10/2013 | Pressler | G06Q 10/10 705/3 |
| 2013/0325510 A1 | 12/2013 | Vendrell | |
| 2013/0326386 A1 | 12/2013 | Vendrell | |
| 2014/0067007 A1* | 3/2014 | Drees | A61N 1/37282 607/46 |

* cited by examiner

FIG. 9

| Specialty | Patient Type | Tasks |
|---|---|---|
| Cardiology | Age under 50 | 1-15 |
| | Age between 50 and 60 | 11-20 |
| | Age over 60 | 11-25 |
| Dermatology | No history of skin cancer | 2, 4, 6, 26-30 |
| | History of skin cancer | 2, 4, 6, 26-35 |
| Pyschology | No family history of mental illness | 1, 3, 5, 37-40 |
| | Family history of mental illness | 1, 3, 5, 37-50 |
| Pulmonology | No history of smoking | 1-8, 51-55 |
| | History of smoking | 1-8, 51-60 |

DIAGNOSIS:

1) Degeneratie disc disease Lumbar spine with radiculopathy.
2) Denenerative arthrisis Right knee.
3) Hypertension.
4) Overweight.

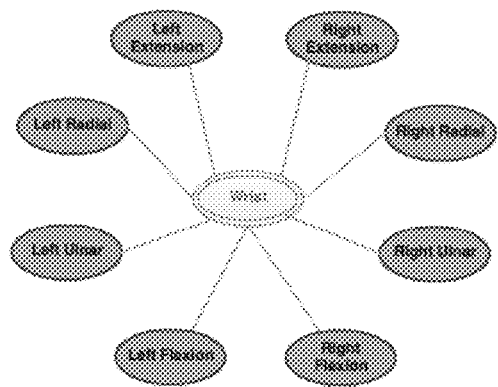
FIG. 16
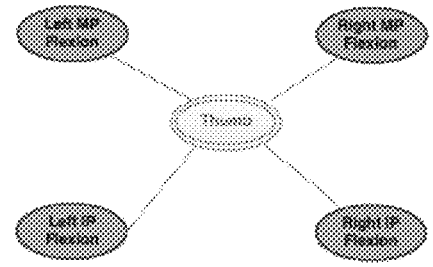
FIG. 17
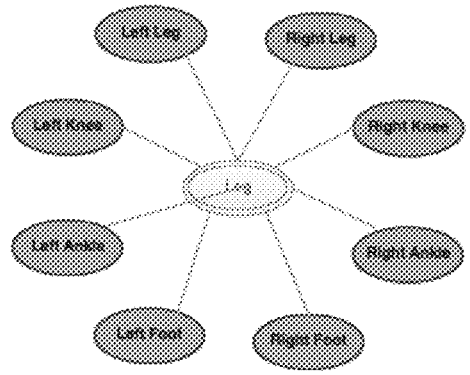
FIG. 18
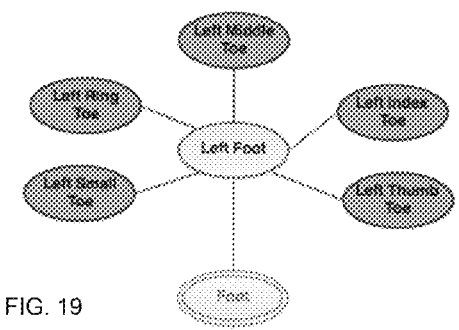
FIG. 19
FIG. 20
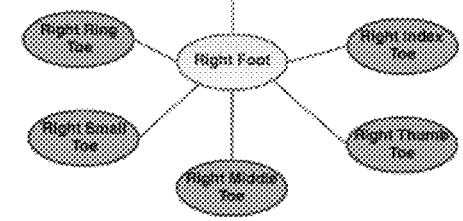

ical patent

METHOD AND SYSTEM FOR GENERATING AN EXAMINATION REPORT

CROSS-REFERENCE TO RELATED APPLICATION

This application claims priority of U.S. provisional patent application Ser. No. 62/017,144, filed Jun. 25, 2014, which is incorporated by reference herein.

FIELD OF THE INVENTION

The present invention relates generally to a method for conducting a physical examination on a patient and generating a data record and a report about the examination, for example a tangible printed report, and a software program or application ("app") that implements the method. In one specific embodiment, the present invention relates to a method enabling a physician to conduct a physical examination using a touch-screen computer such as a tablet, on social security disability applicants and then generate a data record and a report about the examination and a software program or application ("app") that implements the method.

BACKGROUND OF THE INVENTION

Use of computers to create medical reports is now ubiquitous. The medical reports are often created from pre-existing medical data, i.e., data that has already been manually entered into a data record for a patient or is otherwise available in computer-readable form, e.g., a data file, image file and the like.

For example, U.S. Pat. No. 7,899,684 (Fukatsu et al.) relates to a medical report creating apparatus operating in a medical information system to create a report on results of interpretation of medical images that a medical specialist is requested to interpret. The medical report creating apparatus specifies a link corresponding range for strings arranged in an observation column in a medical report display screen. A drag operation is input which specifies contents being displayed on a monitor. When a dragged display icon is dropped onto a link corresponding range displayed portion of a medical report creation screen to specify the string, address information on the content is acquired. The address information on the referenced content is then pasted to the string. Simultaneously, the string in the link corresponding range has its color changed and is underlined for identification. After the report has been completed, a file is saved and the series of operations are finished. The file may be transferred to an image interpretation report requester.

Also, U.S. Pat. No. 8,630,842 (Sorkey et al.) describes techniques for electronically recording notes and other data regarding care that has been provided to a patient in a healthcare setting. The systems and techniques may be used to allow a caregiver to enter information with a minimized number of mouse-clicks, selections and other operations. A contextual graphical user interface (GUI) is provided in the form of a plurality of zones, where each zone includes an iconic representation of a healthcare-related object. One zone may include subjects, in the grammatical sense, and another modifiers, while a third zone displays portions of a human body. A healthcare provider may select on a touch screen interface, the subject and modifier and may select a part of the body on which the particular action was performed. As one example, the subject may be an icon that identifies the type of caregiver that performed the action (e.g., resident physician, or nurse), the modifier may be the action performed (e.g., vital sign readings, IV administration, etc.), and the part of the body may be where the action occurred, if appropriate, such as a compression bandage to the patient's left arm. The system may then use a predefined syntax to convert the icon selections to a data representation of the particular activity.

Sorkey et al. thus relates to after-the-fact entry of data about activities performed on the patient.

U.S. Pat. Appln. Publ. No. 20090204421 (Guimaraes) describes a method for creating and editing electronic health records using a touch screen monitor connected to a computer with a central processing unit. The touch screen is divided into fields sized in accordance with a regular human fingertip, wherein each field corresponds to a data element and contains a label. Medical documentation templates are presented in a hierarchical structure. The user is presented with information in a sequential way in accordance with a process written into the electronic health record. Collapsible graphic user interface (GUI) elements are also provided which, once the GUI elements have been selected, retract in an accordion-type manner. User selections of the data elements are received by touching the user selections in sequence in the field three times. The first touch activates the data element indicating a positive response, the second touch indicates a negative response, and the third touch resets the data element.

SUMMARY OF THE INVENTION

A method for conducting an examination of an object including a plurality of specific tasks using a computer includes displaying on a touch screen, a plurality of designated content areas each representing a respective segment, and then monitoring touch of the touch screen using a touch conversion unit in the computer to determine when one of the designated content areas representing a segment is tapped and when it is determined by a processor that one of the designated content areas representing a segment is tapped, changing the display on the touch screen and displaying on the touch screen, a plurality of designated content areas each representing a respective sub-segment. Touch of the touch screen is monitored to determine when one of the designated content areas representing a sub-segment is tapped and when it is determined by the processor that one of the designated content areas representing a sub-segment is tapped, the display on the touch screen is changed to a plurality of designated content areas each representing a respective task. Touch of the touch screen is monitored to determine when one of the designated content areas representing a task is tapped and when it is determined by the processor that one of the designated content areas representing a task is tapped, the display on the touch screen is changed to instructions to enable performance of the task. Data entry relating to performance of the task on the object or a condition, property or characteristic of the object is accepted using any type of user interface, the entered data is stored in a memory component, and a report is generated from the entered data which preferably entails automatically generating text and/or graphics from completion of performance of each task and including the generated text and/or graphics in the report.

In one embodiment, after accepting data entry relating to performance of the task on the object or a condition, property or characteristic of the object, touch of the touch screen is monitored to determine when an add data icon indicative of a desire to add data to a virtual clipboard is tapped and when it is determined by the processor that the add data icon is tapped, data associated with the display on the touch screen at the time the add icon data is touched is added to a virtual clipboard. When using the clipboard, generation of the report entails selecting data from the clipboard for insertion into pre-existing templates obtained from the memory component.

Display of instructions to enable performance of the task may entail displaying a pop-up window containing at least one of textual instructions and pictorial or graphical images, or a video, about the task and instruments and/or tools needed to perform the task.

In some embodiments, two visually different buttons are displayed on the touch screen simultaneous with each designated content area representing a respective task, e.g., in different colors or shapes. One button indicates performance of the task with normal results and the other indicates performance of the task with abnormal results. The buttons may be displayed adjacent the designated content area. Touch of the touch screen is monitored to determine when the normal button is tapped and when it is determined by the processor that this button is tapped, report text indicating that the task was performed and that all parameters were measured or assessed within normal ranges may be placed in memory in association with the respective task. On the other hand, when the other button is determined to have been tapped, the display on the touch screen is changed to display, for example, an input box having a predetermined phrase or sentence representing the respective task. When this input box is tapped, a keyboard on the touch screen may be displayed to enable data entry of an exception report and/or editing of the predetermined phrase or sentence, and/or a microphone icon may be displayed to enable a speech-to-text dictation function to record the exception report.

Changing the display on the touch screen to display designated content areas each representing a respective sub-segment may entail displaying on the touch screen, a plurality of designated content areas each representing a respective sub-segment in a first level of sub-segments, and then monitoring touch of the touch screen to determine when one of the designated content areas representing a sub-segment in the first level of sub-segments is tapped. When it is determined by a processor that one of the designated content areas representing a sub-segment in the first level of sub-segments is tapped, the display is changed to display a plurality of designated content areas each representing a respective sub-segment in a second level of sub-segments. Again, touch of the touch screen is monitored to determine when one of the designated content areas representing a sub-segment in the second level of sub-segments is tapped and when this occurs, the display is changed to a plurality of designated content areas each representing a respective task.

In one embodiment, non-compliance with all of the tasks may be indicated as a default setting for all of the tasks prior to initiating the examination. The report may be generated with indications of non-compliance with any tasks included in the examination when there is no data entry or activity for the task.

The computer program may be configured to display the plurality of designated content areas each representing a respective segment, monitor touch of the touch screen using the touch conversion unit in the computer, change the display on the touch screen, accept data entry relating to performance of the task, store the entered data in the memory component, and generate a report from the entered data. Also, the computer program may be configured to display screens relating to tasks solely by tapping discrete designated content areas displayed on the touch screen, to thereby enable the report to be generated solely by use of the touch screen.

In one embodiment, performance of a plurality of tasks in a single examination on the same object is enabled, a time and date for performance of each task is recorded, a meta-record containing all of the accepted data and tasks performed during the examination including the recorded time and date of performance of each task is generated and the meta-record is encrypted and archived in the memory component.

In embodiments wherein a plurality of tasks on the same object are performed, a schedule of the tasks to perform during the examination is generated and the touch screen is controlled to display the tasks to perform in accordance with the determined schedule of tasks. This schedule of tasks may be imported into the computer.

Additional monitoring of the touch screen may involve monitoring touch of the touch screen to determine when a help icon indicative of a desire to receive a recommendation relating to the examination is tapped. When this occurs, a recommendation or clinical study results related to the task being performed may be displayed.

Generating of the report from the entered data may entail monitoring touch of the touch screen to determine whether a designated content area for generating a layman's report or a designated content area for generating a physician's report is tapped. When it is determined by the processor that the layman's report generating designated content area is tapped, a layman's report is generated from the stored data and preferably includes data relating to future action by the patient derived from the data obtained as a result of the examination. When it is determined by the processor that the physician's report generating designated content area is tapped, a physician's report is generated from the stored data that is different in content than the layman's report.

When the object subject to examination is human, each of a plurality of medical specialties relating to humans is associated with a different set of tasks from among a larger plurality of tasks, touch of the touch screen is monitored to determine whether a designated content area representing a respective specialty is tapped, and when it is determined by the processor that one specialty designated content area is tapped, display of content on the touch screen displays is controlled to guide the user to perform only the tasks associated with that specialty.

In view of the foregoing method, a computer program may be embodied in non-transitory computer readable media, and configured to implement the method. A computer in accordance with the invention include a processor, a memory component, a touch screen, and computer readable media containing the program that implements the method.

BRIEF DESCRIPTION OF THE DRAWINGS

The following drawings are illustrative of embodiments of the system developed or adapted using the teachings of at least one of the inventions disclosed herein and are not meant to limit the scope of the invention as encompassed by the claims.

FIG. 9 is a table showing the manner in which different workflows can be used in the invention;

FIGS. 16-19 are examples of the hierarchal structure of the program;

FIG. 20 is a key to understanding the hierarchal structure; and

DETAILED DESCRIPTION OF THE INVENTION

Figure 1:
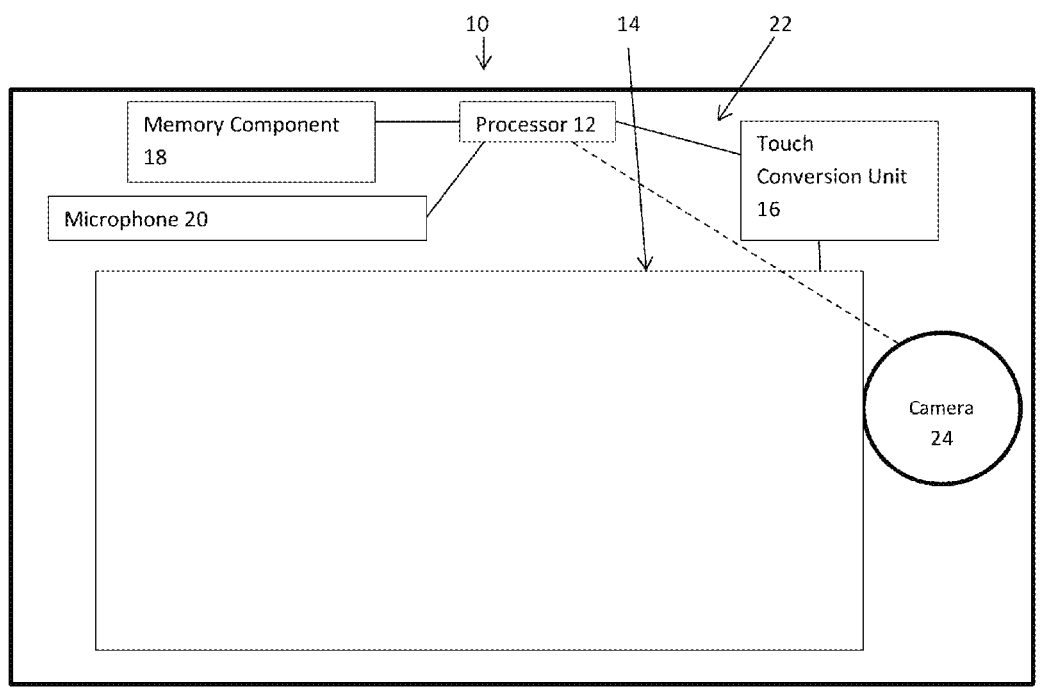
FIG. 1 is a view of a tablet computer that is used to perform the method in accordance with the invention and includes the system in accordance with the invention.

Referring to the accompanying drawings wherein the same reference numbers refer to the same or similar elements. FIG. 1 shows a schematic of relevant parts of a tablet computer 10 that can implement the method for conducting a physical examination for the purpose of creating an electronic medical record (EMR) and generating a report therefrom in accordance with the invention. The tablet computer 10 includes a processor 12, a touch screen 14 with a touch conversion unit 16 that converts the touch by a user on the touch screen 14 into an indication of the location at which the touch screen 14 is touched, and a memory component 18. Tablet computer 10 also includes a microphone 20 on the housing 22 of the tablet computer 10 and which is coupled to the processor 12. Tablet computer 10 also includes a camera 24 on the housing 22 of the tablet computer 10 and which is coupled to the processor 12.

The processor 12 is also coupled to the touch conversion unit 16 and the memory component 18. These components are known to those skilled in the art of tablet computers. Other hardware and software components to enable functional operation of the tablet computer 10 are also present and known to those skilled in the art.

The invention is not limited to any particular construction or configuration of the tablet computer 10 and other types of computers may be used in the invention, including but not limited to laptop computers, smartphones, notebook computers, desktop computers. Such computers would preferably include a touch screen to facilitate entry of information during the physical examination, since the ability to interact with a screen with just a finger press is an important part of the invention.

The tablet computer 10 might also include a discrete keyboard and a cursor control or user interface component such as a mouse. The tablet computer 10 may be any commercial computer such as Microsoft Surface.

Resident in the computer hardware and embodiment on non-transitory computer readable media is a software application in accordance with the invention that is intended for doctors and other healthcare personnel to assist them in conducting a clinical history and physical examination of a patient, generating a report that summarizes both, including a recommendation of plan for further testing, treatment, and follow-up. A novelty of the invention therefore lies in the software application resident in memory of the tablet computer 10 and that can be executed to perform the method and generate a report from input data.

This application may comprise one or more computer programs, preferably resident on non-transitory computer readable media in the housing 22 of the tablet computer 10, but which may also reside at a remote location and be provided to the tablet computer 10 via a network.

The method for conducting a history and physical examination and generating a report will be explained in a basic manner. All of the identified steps in the method are not essential and various subsets of the stages in the method are envisioned.

Figure 2:
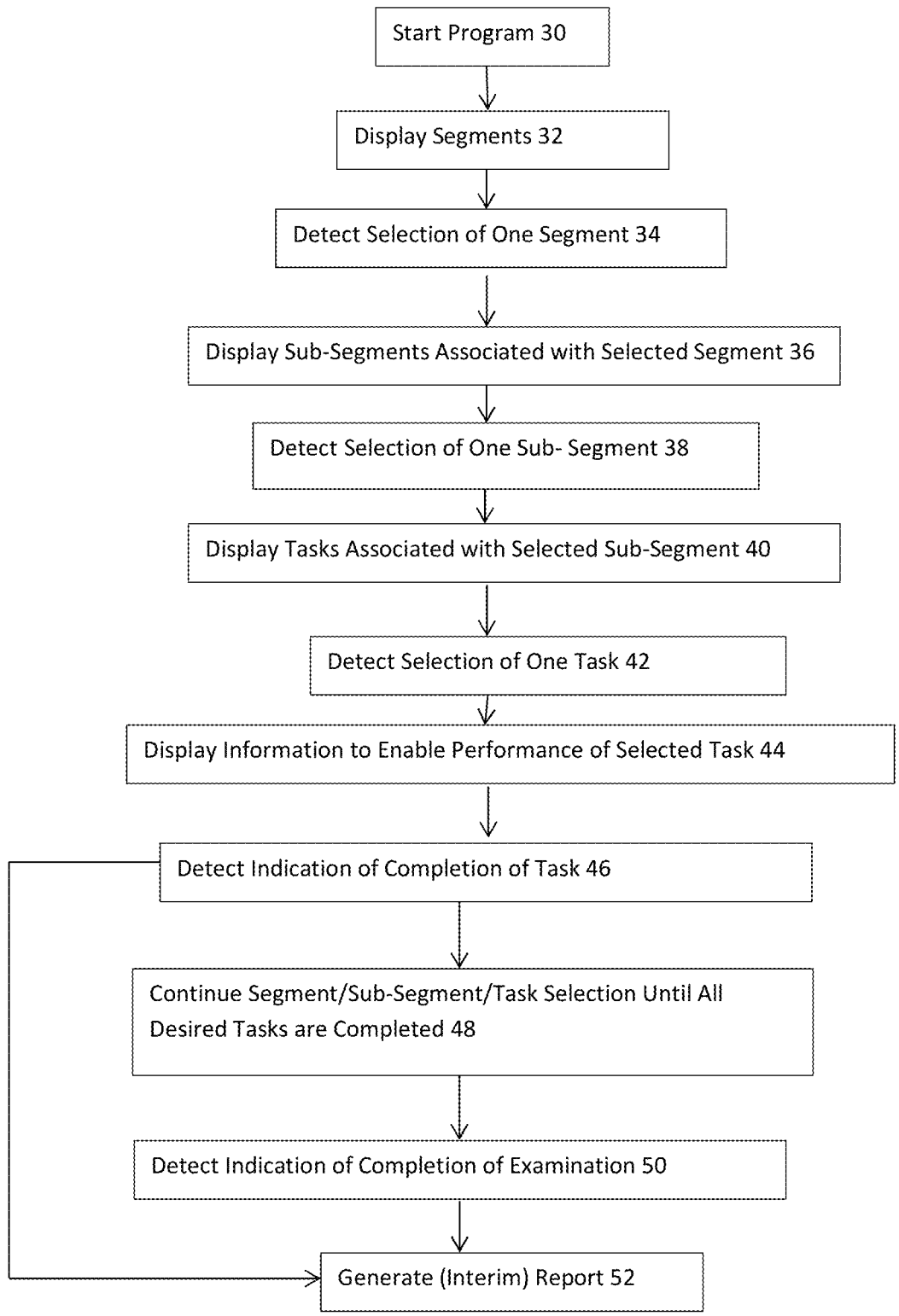
FIG. 2 is a flow chart showing the manner in which a physical examination may be conducted in accordance with the invention.

Referring to FIG. 2 wherein a flow chart of a method in accordance with the invention is depicted, to start, the program is accessed 30 by touching the touch screen 14 at a location where an icon is displayed indicative of the program. The initial stage of use of the program may include security steps, validation steps, identity establishing or confirming steps and other typical steps involved in allowing use of a program to generate an electronic medical record. These steps are not unique to the invention and any known types of routines to achieve these functions may be used with the invention.

Starting of the program causes a series of screens to be sequentially displayed, with each screen enabling the person conducting the physical examination, hereinafter referred to as the user, to enter data about the patient and record exam (or inspection) findings. The examination process is broken into logical segments, sub-segments, and tasks.

Logic underlying the segments is usually topical. That is, to create the hierarchy, the tasks are identified and grouped into specified sub-segments based on commonalities. The sub-segments are then grouped into specified segments based on commonalities. This process to create the hierarchy results in upper level segments that are well-defined and allow the user to understand the expected bottom level tasks in each segment, and then once a segment is selected, the expected tasks in each sub-segment. Thus, it is envisioned that between the upper level segments and the tasks, there may be a single level of sub-segments, or multiple levels of sub-segments. In the former case, selection of a segment reveals a set of sub-segments and from this set of sub-segments, selection of a specific sub-segment directly provides tasks. On the other hand, in the latter case, selection of a segment reveals a set of a first level of sub-segments and from this set of sub-segments in the first level, selection of a specific sub-segment reveals a set of a second level of sub-segments and from this set of sub-segments in the second level, selection of a specific sub-segment in the second level reveals either yet another level of sub-segments or the tasks. There is no limit to the number of levels of sub-segments interposed between the segments and the tasks.

The segments may each have a respective screen, and although a specified order of the segments and sub-segments is provided for the sake of explaining the invention and which generally follows the method physicians are taught and use in daily practice, the order of segments and sub-segments may be customized by the user to suit his/her preferences. Moreover, the user may skip around at random from segment to segment, in any direction.

Thus, in one embodiment, the first screen displayed includes a plurality of segments 32. Selection of one of the segments is detected at 34. This selection causes a new display screen to be displayed that contains a plurality of sub-segments 36. Selection of one of the sub-segments is detected at 38. This selection causes a new display screen to be displayed that contains a plurality of tasks 40. Selection of one of the tasks is detected at 42. This selection causes a new display screen to be displayed that contains information to enable performance of the selected task 44. Completion of the task is detected at 46. This process continues until all desired tasks are completed, which is detected at 48. Completion of the entire examination is detected at 50. A report is then generated automatically at 52, although provision may be made by display of an icon to allow for generation of the report at any time during the pendency of the examination. A partial report may also be generated during the course of the examination, e.g., for interim inspection (see the arrow from task performance completion 46 to generate (interim) report 52.

Generally, when a report is generated, it includes text and/or graphics that is created upon performance of each task during the examination. Completion of a task 46 preferably results in automatic generation of a text string or strings, a sentence or sentences as well. Each task that is completed during the examination thus contributes printed material, whether only text, only graphics (such as graph) or both text and graphics (charts, tables, images) toward a complete report. These text strings are supplied with the software, i.e., included in the memory component 18, but may also be customized by the user so that the report is more in his/her own words.

Automatic generation of a text string or graphics is an important aspect of the program since it involves, stored in the memory component 18 to be accessed by the processor 12, text strings and/or graphics that are associated with specific data entry and available to be retrieved from the memory component 18 by the processor 12 when specific data associated with a task is completed. As such, when a task is completed and data is obtained, the processor 12 is able to insert that data into a coherent text or graphics for inclusion in the report.

As a simple example, the program may be configured to, after the user is directed to take the blood pressure of the patient whose age is known, generate a text that is "The patient's blood pressure is . . . , which is [normal][high][low] for the patient's age", with normal, high or low being determined by the processor 12 from known data about correlation between blood pressure and age. This assignment of the measured blood pressure to a level, or rules to assign a measured blood pressure to a condition, may be modified and revised in the software as medical knowledge and practice changes. The software thus includes an update engine that is configured to receive updates, e.g., via an Internet connection or Wi-Fi, and modify contents of the memory component 18.

As for additional examples of report text generated by the program, i.e., automatically by the processor 12 upon generation of a report requested by the user, the text for a normal examination of the right wrist may read as follows:

The right wrist is negative for deformity, tenderness, impingement, weakness, or swelling.

On the other hand, the text for an abnormal finding, whether the right wrist or another body subject to a task being performed during the examination, may be as follows:

[If the user selects an abnormal finding Y, the text will state the body part and the finding(s) you selected.]

A list may be provided to the user, with different items in the list in individual designated contact areas (e.g., icons or in a drop-down menu), to enable the user to select one of the items for each insert into the pre-configured text simply by touching the touch screen 14. Thus, possible report text includes:

Based on [from the List-first area of pre-configured text], the claimant is not able to [everything in red-second area of pre-configured text]. He/she is able to [everything in green-third area in pre-configured text].

In this case, to obtain this text in the report, the user would be presented with three different lists to view, the specific lists and content thereof would be selected by the processor 12 based on, for example, the task being performed, the characteristics of the patient, the specialty of the examination. The user touches the touch screen 14 to select the items in the lists to be included in the text report and then indicates completion of the selection to enable the processor 12 to move the selected items into the text to be generated when a report is requested.

Similarly, for the following text insertions, the material in brackets could be selected from a list of one or more items provided by the processor 12 and displayed on the touch screen 14 for touch-selection by the user when completing a task, and the user wants to include a description of the task in the report.

Based on [from the List], the claimant can [never] [occasionally] [frequently] [continuously] be expected to use his/her [right] left] hand for [handling] [fingering] [feeling] [pushing and pulling].

Based on [from the List], he/she can [never] . . . be expected to operate foot controls.

Based on the observed range of motion tests and [from the List], the claimant can [never] [occasionally] [frequently] [continuously] be expected to reach overhead with his/her [right] [left] hand.

Based on observations and [findings selected from the List above], the claimant's ability to sit without interruption cannot be expected to exceed [15] [30] [45] [minutes] [1 hour] [2] [3] [4] [5] [5] [6] [7] [8] [hours].

His/her ability to stand without interruption cannot be expected to exceed [15] [30] [45] [minutes] [1 hour] [2] [3] [4] [5] [5] [6] [7] [8] [hours].

His/her ability to walk without interruption cannot be expected to exceed] [15] [30] [45] [minutes] [1 hour] [2] [3] [4] [5] [5] [6] [7] [8] [hours].

The options presented to the user in the examples above are for explanatory purposes only and other options may be presented to the user. Generally, data insertion is controlled by the processor 12 to enable the user to tap the touch screen 14 to select the text insertions with the resultant complete report in easy to read language being automatically generated from the tapped items.

Figure 3:
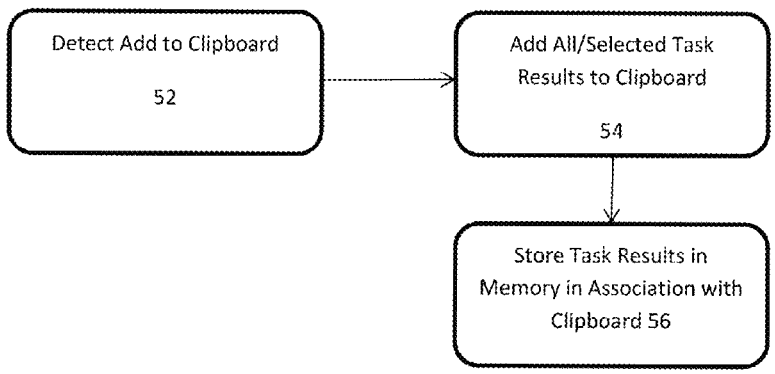
FIG. 3 is a schematic showing the manner in which task results may be added to a clipboard.

Referring to FIG. 3, during or after the process of performing these tasks, the user may send a summary of any or all task results to a clipboard for later reference 54, upon the program detecting an indication by the user to add selected task results to the clipboard 52. The task results sent to the clipboard are stored in a memory component in association with, or with an indication that they are part of, the clipboard 56. The program is thus configured to detect, e.g., touching by the user of an icon indicative of a desire to add data to the clipboard and when present, adds the selected task results of other data input by the user during the examination to the clipboard. The program may thus provide the user with the ability to select specific task results to be added the clipboard once the clipboard addition icon is touched, or the ability to add all obtained task results to the clipboard. In the former case, the program is configured to allow the user to select task results, e.g., touch an icon indicating a desire to have the task result added to the clipboard.

Figure 4:
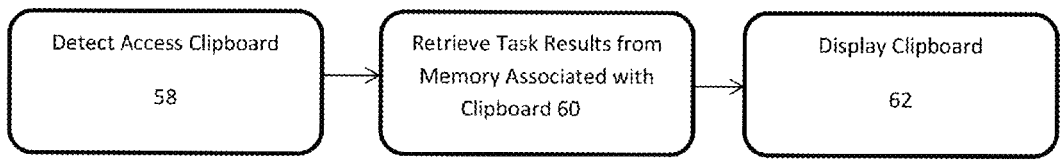
FIG. 4 is a schematic showing the manner in which data on the clipboard may be accessed.

Referring now to FIG. 4, once the clipboard is populated with task results, and the task results are stored in a memory in associated with the clipboard, the program is configured to detect an indication to access the clipboard 58 at any time during its execution. Once such a detection is made, the program is configured to retrieve task results from memory associated with the clipboard 60, and then display the clipboard with the retrieved task results 62. The clipboard can thus be viewed at any time during the history and physical examination, i.e. while the user is conducting the examination and obtaining the patient's medical and clinical history.

The program is also configured to enable the user to reference any or all task results on the clipboard, include them in the final report by marking an indicating icon associated with each task result which is displayed on the touch screen 14, and thus facilitate and/or justify his/her final conclusion (assessment).

As such, the program maintains a "smart clipboard" as the examination is conducted. That is, the clipboard may be populated with task results before the examination is completed and during the course of the examination, i.e., at most, each time a task result is completed, the user can add that task result to the clipboard. The program extracts data from the completed tasks and populates the clipboard with a list of potentially relevant "clinical findings" for future action and/or reference. The user could be trained to populate the clipboard any time a task result is deemed significant, and thus insert the significant task result onto the clipboard for easy reference at a later time. This smart clipboard populates menus provided by the program automatically as the user examines patients. The user may select any of these findings to add to a new examination. The user may also edit or delete the smart clipboard at any time.

To reiterate, as data are collected during the examination, by touching icons representing segments, sub-segments, and tasks, those data which the user believes are important enough to affect the claimant's ability to perform certain functions may be transferred to the clipboard, which is also termed an "Impacting Findings List". At the end of the examination, these data are condensed extracts from the examination, e.g., a subpart of the examination relating to the history and physical examination. They are miniature icons which the user can recognize visually as representing a segment, sub-segment, or task.

This list thus builds as the history and physical examination progresses, i.e., as more and more tasks forming the examination are performed and completed. The user may view it at any time during the history and physical examination, either as a list of icons pressed or as a list of text statements representing the segments, sub-segments, or tasks highlighted during the examination. The clipboard is essential when the user comes to the end of the history and physical examination and has to make one or more final assessments, both to draw assessment conclusions and to justify them.

Figure 10:
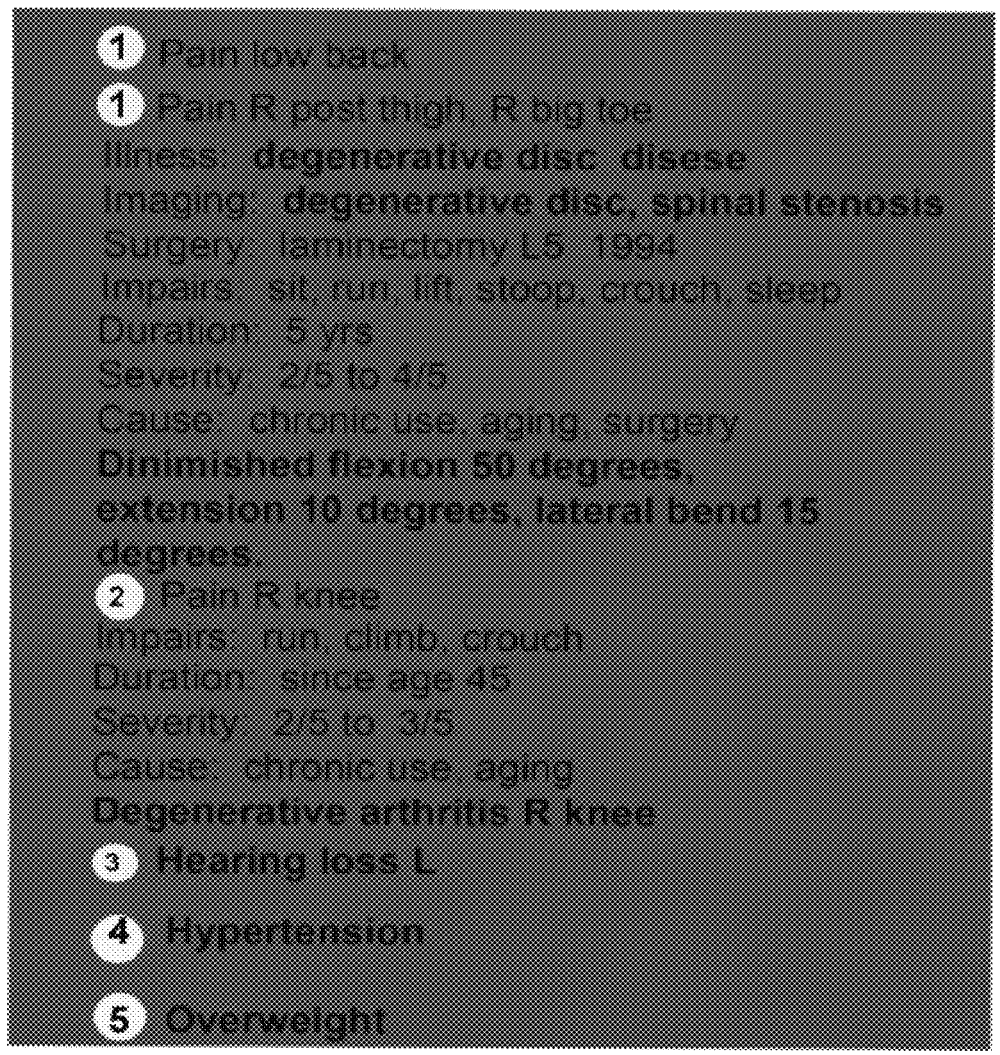
FIG. 10 is a screen shot of a clipboard used to display data of significance obtained or derived during an examination.
Figure 11:
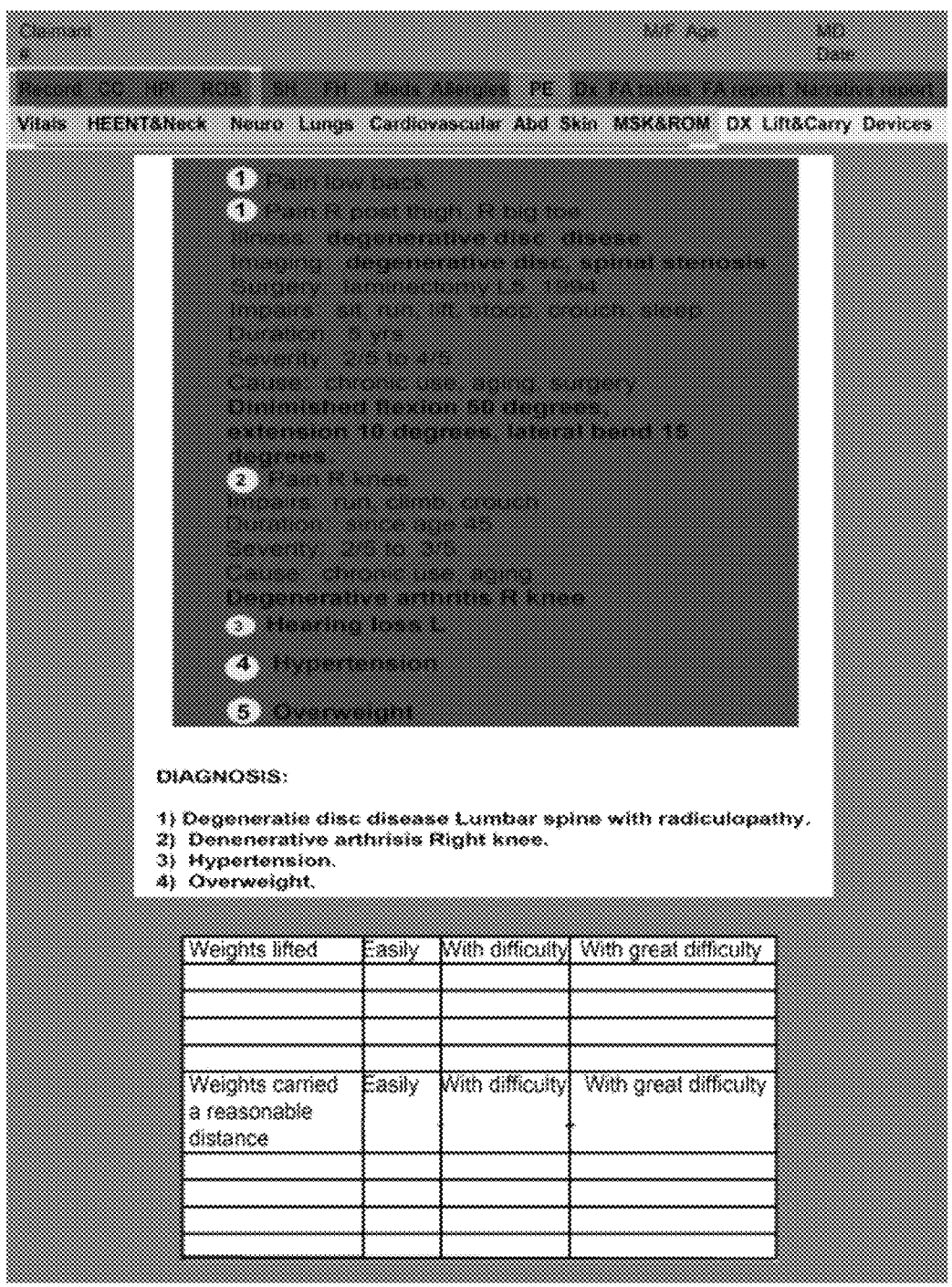
FIG. 11 is another screen shot of a clipboard used to display data of significance obtained or derived during an examination.

The impacting findings clipboard is thus an orderly listing of icons or text that depicts significant findings (data) from the history and physical examination. Samples using text, not icons, are shown in FIGS. 10 and 11, and these screen shots may be displayed on the touch screen 14.

As an example of the use of the clipboard, a functional assessment about the patient being examined may be generated using the program. The functional assessment ("FA") may comprise 8 tables. The program causes display on the touch screen 14 of the impacting findings clipboard above each functional assessment table. The user refers to the impacting findings clipboard and completes the table. To add justification text to the assessment of each table, the user may choose from the impacting findings clipboard. As the impacting findings clipboard moves from table to table, the selections made to justify the table in question are no longer indicated as selected for the next table. Each table deals with specific impairments. Accordingly, the report may be generated by selecting data from the clipboard for insertion into pre-existing templates obtained from the memory component 18, which process is facilitated by the processor 12. The specific template(s) may be determined by the user for the specific examination or recommended by the software based on the type of examination (the specialty) or the task that have been performed.

These impairments draw on specific impacting findings relating to the functional abilities or capabilities of the patient. For example, the findings may be as follows:

Based on [Finding inserted from the Clipboard], the claimant is not able to [everything in red]. He/she is able to [everything in green].

Based on [Finding inserted from the Clipboard], the claimant can [never] [occasionally] [frequently] [continuously] be expected to use his/her [right] left] hand for [handling] [fingering] [feeling] [pushing and pulling].

As mentioned above, the material in brackets could be selected from a list of one or more items provided by the processor 12 and displayed on the touch screen 14 for touch-selection by the user when completing a task, and/or data that has previously been sent to the clipboard during the performance of the task. Also, the use of color in the pre-existing templates to generate the report may be varied from the colors shown, or other visually distinctive techniques may be used in the invention without deviating from the scope thereof.

In one implementation, the user would progress through the various segments, starting with patient history, then physical examination and then functional assessment. In this regard, one of the segments may be a patient history segment. An indicator is displayed on this screen to allow the user to proceed to the next, second screen when entry of historical information about the patient is complete. The second screen is a physical examination segment screen. An indicator is displayed on this screen to allow the user to proceed to the next, third screen when entry of information about the patient's physical examination is complete. The third screen is a functional assessment segment screen.

From the patient history segment screen, the user is provided with options for specific entry of data about the history of the patient, these more specific options representing sub-segments. These sub-segment options include: 1) Chief Complaint; 2) Review of Medical Records; 3) History of Present Illness; 4) Past Medical History; 5) Review of Systems; 6) Social History; 7) Family History; and 8) Medications and Allergies.

From the physical examination segment screen, the user is provided with options for specific entry of data about the physical examination of the patient, these more specific options representing sub-segments. These sub-segment options include: 1) Vital Signs; 2) Head, ears, eyes, nose, and throat/neck; 3) Neurological; 4) Lungs; 5) Cardiovascular; 6) Abdomen; 7) Skin; 8) Musculoskeletal with Range of Motion; 9) Lift and Carry Test; and 10) Assistive Devices.

From the functional assessment segment screen, the user is provided with options for specific entry of data about the functional assessment of the patient, these more specific options representing sub-segments. These sub-segment options include: 1) Lift/carry; 2) Sit/stand/walk/cane; 3) Hands; 4) Feet; 5) Posture-related; 6) Hearing, vision and speech; 7) Environmental limitations; 8) Personal living activities; and 9) Other impairments.

Within each of the sub-segments, there are one or more tasks that require input from the user about the patient that are obtained during the course of the examination. The user may ask the patient for information to complete a task, or complete a task by performing a known interaction with the patient to obtain the data, e.g., take their blood pressure or pulse, determine a reflex, etc. Thus, from the sub-segment screens, the user is provided with options for selection of tasks associated with the respective selected sub-segment, and can select one of the tasks at each time to perform.

Accordingly, the program is configured to monitor touch of the touch screen 14 using the touch conversion unit 16 in the computer 12 to determine when a designated content area (icon) representing a specific task is tapped and when it is determined by the processor that one of the designated content areas representing a task is tapped, the display on the touch screen 14 is changed under command of the processor 12 to displaying on the touch screen 14, instructions to enable performance of the task. These instructions may be in the form of written information or directives to take steps and interact with the patient to obtain the data needed to complete the task.

Alternatively, the software in accordance with the invention is configured to show pictorial instructions for performing the task, or a video instruction option. That is, the user may be presented with a series of images or a video including the instrument(s) being used to perform the task and/or the part of the patient being examined or on which the task is to be performed and visually guided in the performance of the task. The instructions could also identify tools, instruments and/or materials needed to perform the task. Generally, the instructions for task performance encompass displayed content on the touch screen 14 whether in written text form or visual graphical form. Moreover, it is also possible to include oral instructions alone or in combination with the written and visual instructions.

For data entry when any of the segment, sub-segment or task screens are displayed, the program allows for numerical inputs using a number pad similar to an on-screen keyboard. The display of an on-screen keyboard on the touch screen 14 and the manner in which letter entry into the virtual keyboard is converted by the touch conversion unit 16 into text is known to those skilled in the art to which this invention pertains. Graphical sliders or animated body part illustrations may also be employed for numerical input. The sliders or body part illustrations are moved with a finger (or stylus or mouse or keyboard arrow keys) to increment or decrement a displayed base number.

In the segment, sub-segment and task screens that are displayed, the program is configured to display icons on the touch screen 14 with indicia thereon that respond to touch. Each icon causes a different response depending on the associated indicia. Touching one icon may cause a plurality of additional icons to be displayed, and so on. A hierarchy of fields for data entry is used by the program. The first level of icons may be considered the segments, the second level of icons may be considered the sub-segments and the third level of icons considered the tasks. Tasks may also be included in the first and second levels of icons.

Icons are used herein as an example of a designated content area whose touch causes a desired result related to the content of the area being designated. Instead of icons, the computer program may be configured to display other types of designated content areas in different formats. For example, the computer program may be configured to display the segments in a drop-down menu, the sub-segments in another drop-down menu and the tasks in yet another drop-down menu. In the same interacting manner as with icons, the user only has to touch, e.g., an arrow, associated with the drop-down menu in order to view the contents of the menu and then touch one of the segments, sub-segments or tasks that appear. Use of drop-down menus instead of icons, and other designated content areas known to those skilled in the art to which this invention, also are considered to be within the scope of the invention.

The icons are digitally active, readily recognizable, and selectable on the touch screen 14, and optionally animated, and thus represent the segment, sub-segment, or task at hand. For example, there are icons that represent inspection tasks.

An important aspect of the invention is that at least some, and possibly all, of the icons do not require dragging to cause a response. Rather, a tap on the icon when visible on the touch screen 14 causes an appropriate, different screen to be displayed, dependent on the indicia associated with the icon. The following screen may include data fields for entry of data, e.g., by tapping the data field and then touching a virtual keyboard displayed on the touch screen 14.

Color is used to highlight issues that arise during the physical examination being conducted using the program. Each icon has both a green ("normal") and red ("abnormal") button associated with it (see FIG. 15 described below). Touching the icon itself typically generates a pop-up window with information about the task, best clinical practices and recent research data, written, visual, pictorial and/or graphical instructions about how to perform the task and other options such as user customization. Different colors may be used instead of green to indicate a normal condition and red to indicate an abnormal condition.

Touching the green button associated with an icon will generate report text stating that the task was performed and that no issues were identified, i.e., all parameters associated with the task were measured or assessed within normal ranges.

Touching the red button associated with an icon causes an input box to appear on the screen. A predetermined phrase or sentence preferably appears in the text box, representing the task selected. Touching inside the input box causes an on-screen keyboard to appear so that an exception report can be made and/or the predetermined phrase can be edited. Touching a microphone icon causes a speech-to-text dictation function to record the exception report, i.e., via microphone 20.

Instead of using color to differentiate the buttons, other visually different buttons may be used. For example, two different shaped buttons may be provided, and the user informed that one shape is indicative of an uneventful, normal task performance and the other shape is indicative of the need to create an exception report indicative of an issue that needs to be addressed as a result of the performance of the associated task in the examination. Different shaped buttons may also be colored differently. Basically, any technique to enable the user to easily identify the appropriate icon to touch may be used, whether color, shape or a combination.

Other icons and functions associated with the text box include a sound recorder for speech dictation and/or sound capture, and a camera button to record images and/or video (which may be possible using the camera 24 on the tablet computer 10). Another configuration could include a live consult button for two-way video or voice discussion with a remote party, e.g., supervisor or technical support staff.

Another configuration and input option is a drop-down menu of custom text selections. Each text selection would be associated with a segment, sub-segment, and task, and could be pre-populated by the employer and/or customized by the user.

Figure 5:
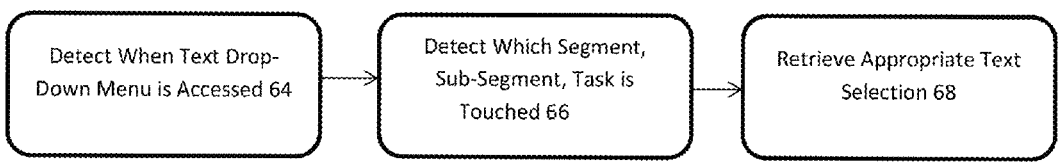
FIG. 5 is a schematic showing the manner in which a pre-existing text selection can be accessed.

Referring to FIG. 5, and additional to the description above about text insertions into the report, the custom text selections are included in the software program and each is associated in the memory component 18 with a particular segment, sub-segment or task. A correspondence between the segment, sub-segment and task to the text selection is contained, e.g., in a table, and accessed by the processor 12 when the user touches the drop-down menu to retrieve one of the text selections, The program is thus configured to detect when the drop-down menu is accessed during use of the program 64, and once detected, detects which segment, sub-segment or task is touched 66, and then once touch of a specific segment, sub-segment or task is detected, accesses the memory component 18 to retrieve the corresponding text selection 68.

Figure 6:
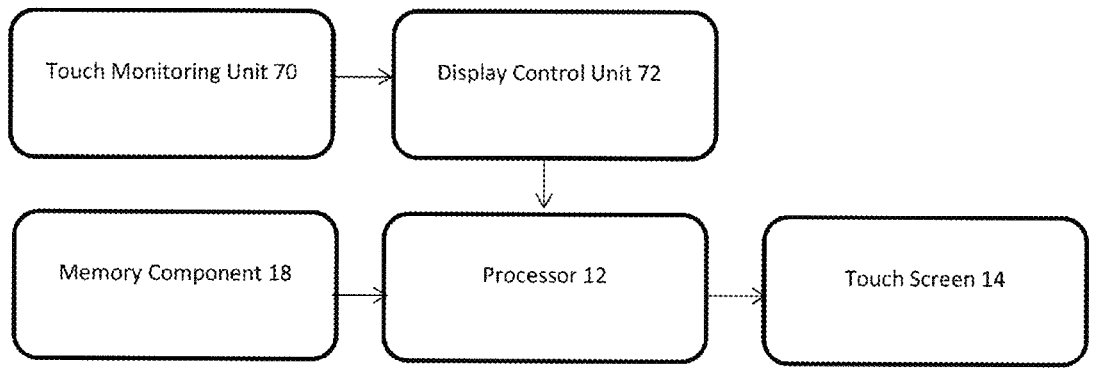
FIG. 6 is a schematic showing structure that effects the selection of pre-existing text by touch in accordance with the invention.

A schematic of the componentry that achieves this text selection is shown in FIG. 6 and includes a touch monitoring unit 70 that monitors the touch screen 14 for detection of an intent to access the drop-down menu of text selections. The touch monitoring unit 70 may be implemented as a software program or subroutine. A display control unit 72 is coupled to the touch monitoring unit 70 and controls the touch screen 14 to change the content being displayed on the touch screen 14 based on the part of the touch screen touched by the user. The display control unit 72 is coupled to the processor 12, in turn coupled to the memory component 18 (see also FIG. 1), to enable the display control unit 72 to be provided with the appropriate text selection for display.

An advantage of the use of a drop-down menu to enable selection of pre-existing text, is that text generation thereby does not require entry of text by the user. Rather, the selection of pre-existing clauses of text is automatic. The software also automatically applies rules for correct gender, tense, case, grammar, and syntax so that the final written report is consistent and grammatically correct.

As an example, after initial entry of data about the patient and intake relating to the current complaint of the patient, the user can access the drop-down menu during the examination to obtain text as follows (the material in brackets indicate data entered by the user or data generated using the touch entry system of the invention):

[Claimant name] states that he/she has [condition], which began [date]/[when he/she [was _____ years old]/ [_____ months/years ago], due to [an injury] [an illness] [chronic use] [aging] [surgery] [a condition at birth] [exposure to a toxin] [text]. The condition has lasted [_____ months/years] and has [worsened] [not changed] [improved]. He/she rates the severity of the condition as [_____] out of 5.

This text entry can also form the basis for a report, provided in the form of an e-mail to another physical or health professional, an electronic medical record entry, a printed report, and the like.

As the user moves through the examination/inspection tasks, the program accumulates report text based on user input for the various segments, sub-segments, and tasks entered via steps 32-46. At any time during the process, the user can view the assembled report text and also get a sense of how much of the examination/inspection has been completed (% of tasks).

The default setting for all segments, sub-segments, and tasks is "not examined." If the user does not touch a red or green button for a segment, sub-segment, or task, the program will generate report text stating that the segment, sub-segment, or task was not examined or inspected.

The program can also prompt for suspicious data entries that appear to be out of range for a typical reading with a pop-up warning asking the user, "Are you sure? The typical range of values for this task is x to y." Similarly, the program can monitor for inconsistent inputs made in different segments or sub-segments of the program and generate a question to the effect, "Are you sure? You entered xxx for Task YYY. That entry is inconsistent with your input for this task." Affirmative entries (overrides) are then recorded in the program database. "Are you sure?" notifications can also be generated for segments and sub-segments that the user left blank, i.e., not asked or examined.

As each segment, sub-segment, or task is completed, the corresponding icon on a menu bar is marked so that the user can see it has been completed.

Once all sections have been completed, the user is presented with the option to view a draft report 50 from the information entered in the various segment, sub-segment or task screens in steps 32-46.

For this step, a full examination report is generated with proper spelling, grammar, and syntax. The report may also contain charts, tables, sound recordings, photos, and videos entered in any of the segment, sub-segment or task screens. The report may be stored in the memory component 18 on the tablet computer 10, transmitted from the tablet computer 10 to another computer by e-mail or to be stored in the cloud, and printed into tangible form by a printer connected to the tablet computer 10.

The user can make edits as desired to the draft report. The program tracks all edits and stores them in a database in memory component 18. All of the edits as well as all of the data entered during the examination/inspection process are saved in a file separate from the examination/inspection report, for archival and auditing purposes.

When generating the examination report, the processor 12 is configured to perform an analysis of the entered data about the patient and derive a conclusion or assessment subject to the physician's modification and/or approval. The processor can use the data populating the clipboard (discussed with respect to FIGS. 3 and 4). The processor 12 can also be configured to determine a plan for further testing, treatment, and follow-up, again subject to the physician's modification and/or approval. This plan may be presented in written form in layman's terms for the patient with specific recommendations and actions to be taken, i.e., diet, exercise, lifestyle, medication.

Figure 7:
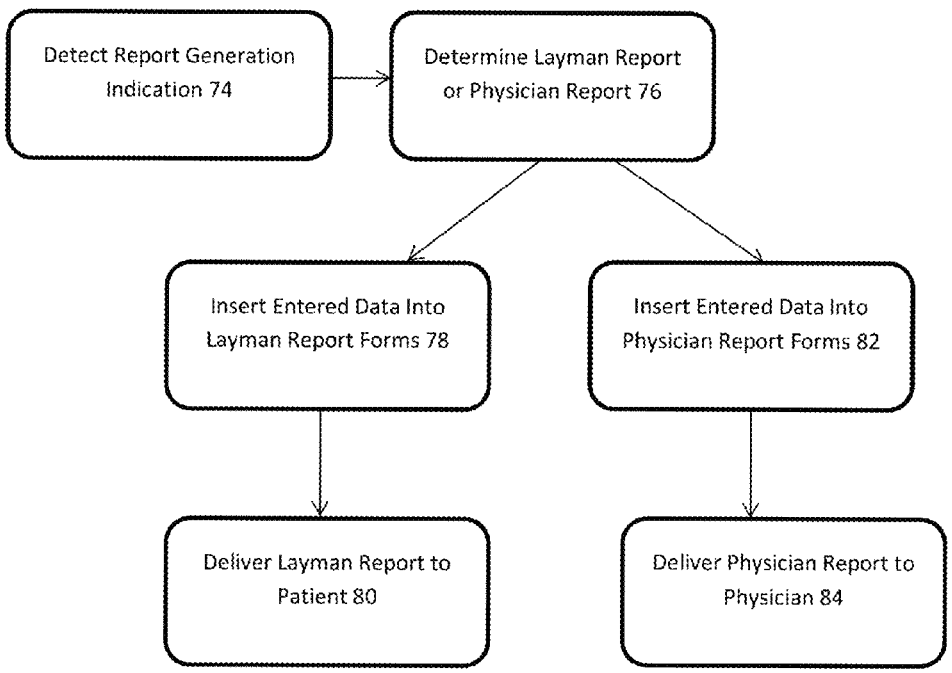
FIG. 7 is a schematic showing the manner in which a report is generated in accordance with the invention.

FIG. 7 shows the manner in which the program in accordance with the invention analyzes the data and generates one or more reports, as determined by the user. The program is configured to detect an indication by the user to generate a report 74 and then determine whether the user selects to generate a layman's report or a physician's report 76. If the program detects that the user wants to generate a layman's report, then the program inserts the entered data into layman report forms 78 and deliver the layman's report to the user, who will then deliver it to the patient 80.

The layman's report would typically include a written summary of the exam in readily understandable terms with specific patient-specific recommendations and actions to be taken by the patient, which presumably relate to diet, exercise, lifestyle, and/or medication. The recommendations and actions are derived by the processor 12 in consideration of the entered data about the patient's history and the intake from and about the patient obtained during the examination.

If the processor 12 determines that the user wants to generate a physician's report 76, then the program inserts the entered data into one or more physician report forms 82 and delivers the layman's report to the physician 84. In this case, as well as when the layman's report is delivered to the patient, the delivery may be electronic, e.g. via e-mail, posted to a secure dropbox or in the cloud, or printed out and handed, mailed or otherwise physically delivered to the patient or physician.

Figure 8:
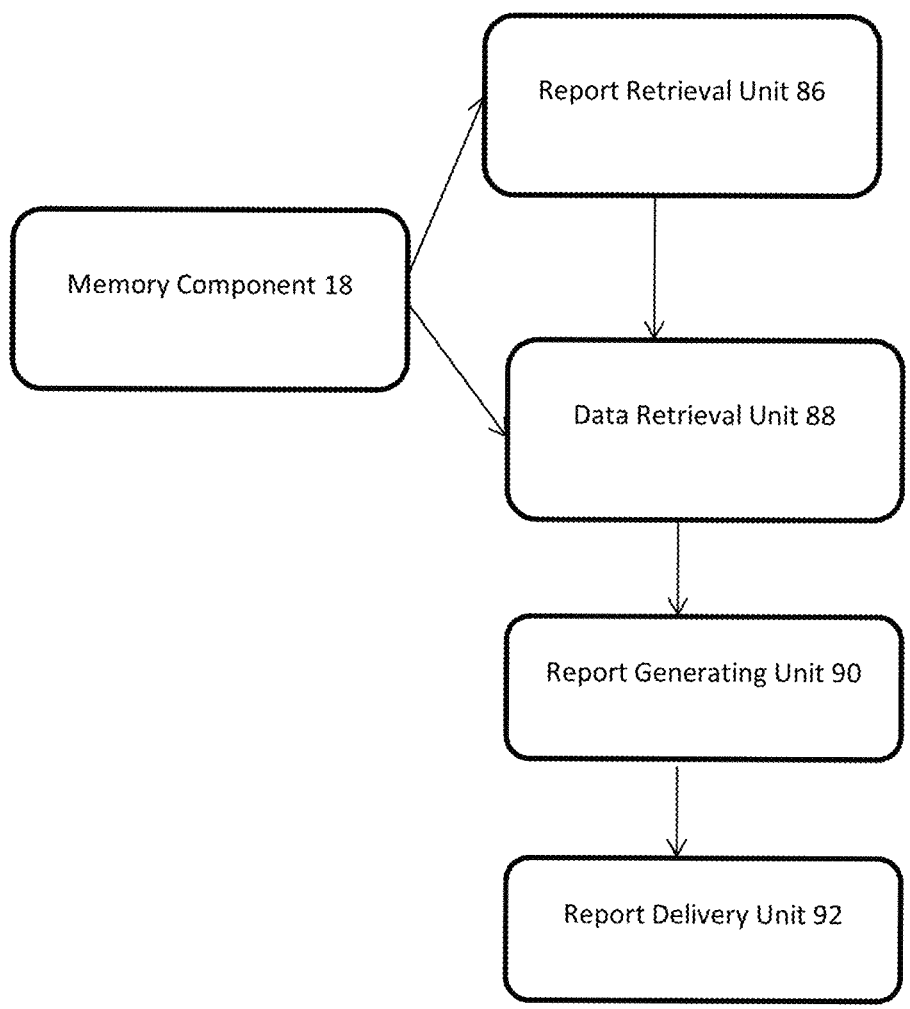
FIG. 8 is a schematic showing structure that effects the report generation in accordance with the invention.

A schematic of the componentry that achieves the report generation is shown in FIG. 8. This componentry may be hardware and/or software and reside in the tablet computer 10. The report retrieval unit 86 cooperates with the memory component 18 to retrieve the forms upon selection by the user to be populated with data about the patient or other object being examined at that time. The data retrieval unit 88 also cooperates with the memory component 18 to retrieve data dependent on the form selected. Different forms include different sets or subsets of data and therefore once the form is selected by the user, the data required to complete the form is determined and retrieved. To this end, each form may include an indication of which data is needed for its completion and then once selected, the processor 12 considers this and retrieves the appropriate data about or relating to the examination just completed.

The form and data is provided to the report generating unit 90 which generates the report. The report generating unit 90 fills in the forms with the data in the appropriate locations, whether the form is a layman report form or a physician report form. The report delivery unit 92 then delivers the report to the laymen and/or physician, e.g., by e-mail, mail, text message, etc.

The program can be customized by the user. The user may change background colors, move tasks into different sequences, and enter custom text phrases or sentences to be used in place of or as an alternative to the stock sentences and phrases that come with the program. The standard configuration may also be modified by an employer to add/remove tasks, change workflow to reflect corporate policies and procedures, add corporate identity, and to enable/disable customization of various features by the user.

Referring back to FIG. 2, one of the sub-segments available in patient history is a Family History (FH) and Social History (SH) icon. Although possibly together in a single icon, two separate icons may be provided for the Family History and the Social History. Generally, by selecting the icon, a window will open with data fields for entry of information about the patient's family history, i.e., information about relatives of potential relevance to the current examination. For example, data about other family members with a history of the same issue may be entered, or simply field to enable entry of a relative, i.e., their relationship to the patient being examined, and one or more diseases or conditions they have or had. This data entry may be made via the touch screen 14, or a keyboard visually displayed on the touch screen 14 (which virtual keyboard display may be effected by the processor 12 in a manner known to those skilled in the art to which this invention pertains).

Similarly, the Social History icon may be accessible from the Family History icon and when selected, a window will open with data fields for entry of information about the patient's social history, i.e., information about friends of potential relevance to the current examination. This data entry may be made via the touch screen 14, or a keyboard visually displayed on the touch screen 14.

Another icon provided by the software program as a sub-segment of patient history is a Medications and Allergies icon. Although possibly together in a single icon, two separate icons may be provided for the Medications and Allergies. Generally, by selecting the Medications icon, a window will open with data fields for entry of information about the patient's current medications, i.e., information about medicine the patient is currently taking. The Allergies icon may be accessible from the Medications icon and when selected, a window will open with data fields for entry of information about the patient's allergies. Data entries about medications and allergies may be made via the touch screen 14, or a keyboard visually displayed on the touch screen 14. Data may also be entered via voice dictation, e.g., by speaking into the microphone 20 on the tablet computer, which is coupled to the processor 12 with the microphone 20 or processor 12 providing for speech recognition.

After information about the patient's family history, social history, medications and allergies has been entered, it is easily viewed by touching the appropriate icon. The information is stored in the memory component 18 by a data storage program being executed by the processor. This data storage program organizes the storage of data in association with the respective field and when a data presentation program is executed by the processor 12, the data is retrieved from the memory component 18 and displayed on the touch screen 14 for viewing by the person conducting the physical examination. Lists of data, typically, clinical findings, are stored on the tablet computer 10 for subsequent examinations of other patients. Data is thus accumulated for future selection from smart menus that become customized to the user's experience over time. The user at any time may modify or delete any or all data from these lists.

Additional customization is provided by the program that is configured to allow the workflow to be tailored and customized to different types of examinations and different patients when the object subject to the examination is, for example, a human. FIG. 9 shows a table of different medical specialties and different types of patients and a list of numbered tasks that would be included in the workflow for different combinations of specialty and patient type. The patient type may be based on age, medical history and/or family history. The numbering of the tasks is for explanatory purposes only and each may represent a task to be completed using the program. This customization optimizes use of the program since inappropriate tasks for a specific specialty type of examination or for a specific patient type are not included in the workflow for that patent when being examined by a specialist.

For this functionality, the computer program would be configured to be able to direct the performance of a large number of tasks for multiple specialties. However, not all of the tasks are performed in every examination. Rather, only a subset of the tasks is performed in each examination, dependent on the specialty of the examination. For example, for a cardiological examination, specific tasks relating to the heart health of the patient would be presented to the user to complete, as opposed to tasks relating to movement of the foot, which would be more appropriate for presentation during a podiatric examination.

Thus, the program is configured to include in memory, software or subroutine to direct performance of a large number of tasks. Each medical specialty is associated with a different set of tasks from among the plurality of tasks (see FIG. 9). Then, during use of the program, after the user initiates the program, the program can be configured to display on the touch screen 14, the available specialties, e.g., with tabs or in a drop-down menu, The touch screen 14 is monitored to detect when one of the specialties is tapped, and when such a tap is detected, the content of the displays on the touch screen 14 are controlled to guide the user to perform only the tasks associated with that specialty.

The program in accordance with the invention can also be designed to import an outline of the workflow and convert it into an examination framework. The workflow represents a schedule of tasks to perform when conducting the examination. It is thus possible to provide the program with direction to manage the display of the different tasks on the touch screen 14 for the user when conducting an examination using the tablet computer 10.

Each examination conducted using the tablet computer 10 generates a "meta-record" containing all of the information obtained and actions taken during the examination. The meta-record also includes the time and date of performance of each task, which may be recorded in the memory component 18 in association with the indication of completion or performance of the tasks. The meta-record can be encrypted and archived for auditing, quality control, or reconstruction purposes, e.g., in the memory component 18.

Instead of being used during a physical examination of a patient, the application and tablet computer 10 may be used to conduct an inspection in other industries, for example: housing and construction; structures or infrastructure such as dams, bridges, highways, commercial and government buildings; machinery; transportation equipment such as automobiles, trucks, trains, buses, ships and boats; military equipment;

airplanes and other aerospace equipment; animals; and geographic landmarks such as lakes, rivers, streams, volcanos. As such, when used herein, an "examination" is not limited to an examination of a human's physical condition and encompasses examination of other items. Of course, it is understood that the segments, sub-segments and tasks for each examination would be different. The specific segments, sub-segments and tasks for each examination may be tailored to the specific object being examined.

The technique underlying the application would be the same. That is, the application for examining the object would provide an organized hierarchy of tasks, organized into segments and sub-segments, tasks to perform in each sub-segment, and the user-driven extraction of data to a clipboard for use in generating the final assessment/report. Arriving at the task to perform may be achieved solely by touch, i.e., the user taps an icon indicative of one segment from among a plurality of icons indicative of different segments displayed simultaneously on the touch screen 14, and this touch causes another display of a plurality of icons indicative of sub-segments, The user touches an icon indicative of one sub-segment from among a plurality of icons indicative of different sub-segments displayed simultaneously on the touch screen 14, and this touch causes another display of a task to perform as part of the examination. The color coding of the icons or buttons associated with the icons is used to conduct the examination.

A generic computer program to perform the examination would be configured to display on the touch screen, the plurality of icons each representing a respective segment, sub-segment and then task in sequential order, to monitor touch of the touch screen to detect touching of the icons using the touch conversion unit in the computer, change the display on the touch screen based on detected icon touch, accept data entry relating to performance of the task, store the entered data in the memory component, and generate a report from the entered data. This computer program may be advantageously configured to display screens relating to tasks solely by tapping discrete icons displayed on the touch screen, to thereby enable the report to be generated solely by use of the touch screen. Dragging of icons is not required to generate the report. Moreover, the touch screen capability is utilized advantageously to enter patient data, as opposed to merely arranging patient data that has already been entered.

Throughout the program and the displays being presented on the touch screen 14 by the processor 12, there may be a help icon. When touched by the user, the help icon may open another window that contains updated recommendations and the latest clinical study results for specific topics related to the examination. An indication of the content of the recommendation or clinical study may be included in the icon to assist the user when conducting the examination. The icon could indicate that there is another recommended task for the user to conduct based on a clinical study or recommendation. The user can thus be guided in the examination to conduct additional tasks based on clinical studies the user may not know about.

Figure 12:
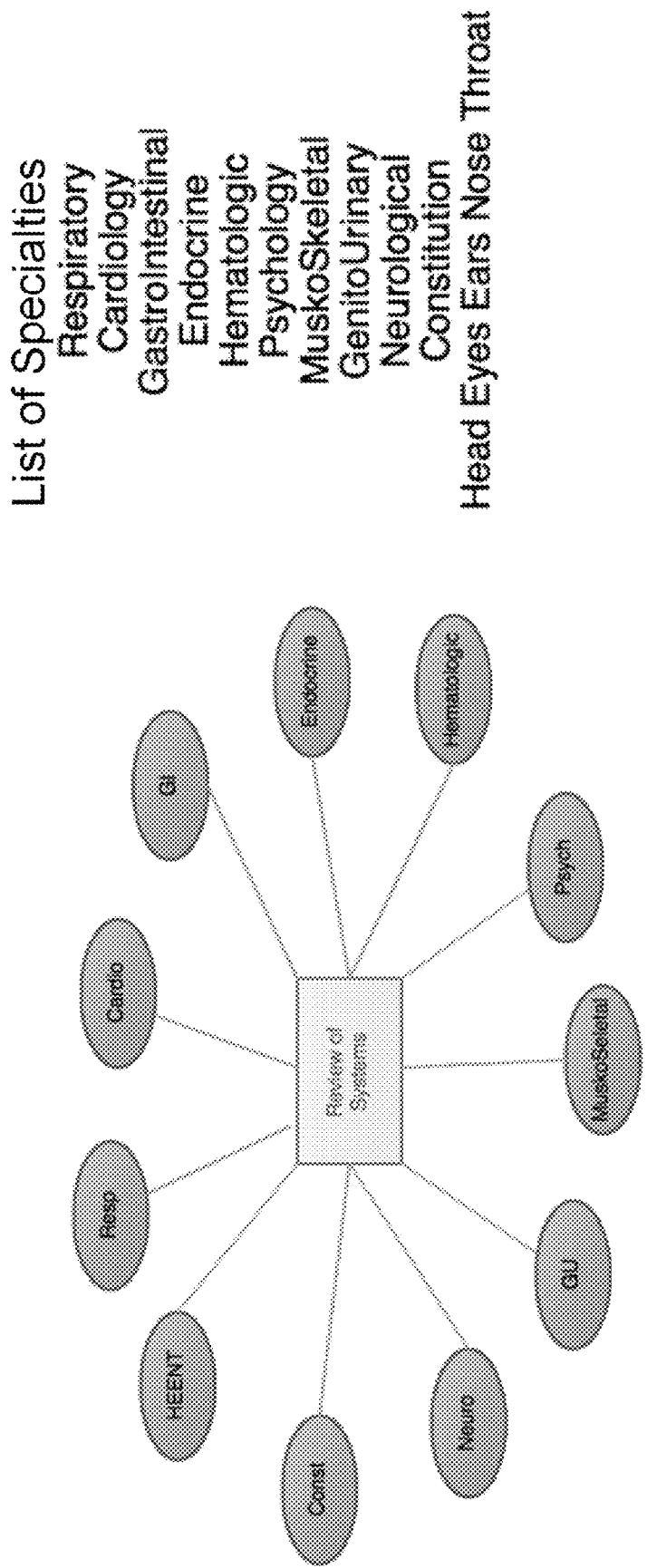
FIG. 12 shows a display on the touch screen at an initial stage of the examination of human patient.

Referring now to FIG. 12, an initial screen display on the touch screen 14 may include a centrally located "Review of Systems" icon with an icon or designated contact area linked to this central icon and each containing a respective specialty type of examination. An exemplifying, non-exclusive list of specialties is set forth and contains respiratory (Resp), cardiology (Cardio), gastrointestinal (GI), endocrine, hematologic, psychology (Psych), musculoskeletal, genitourinary (GU), Neurological (Neuro), constitution (Const), and head eyes ears nose throat (HEENT). From this initial screen, which may represent sub-segments that can be selected to obtain a displayed list of possible tasks to perform in connection with each specialty type of examination, or to obtain a displayed list of sub-segments that generalized groups of tasks (whose selection in turn will cause display of actual tasks), the user can access tasks to perform for the selected specialty.

Figure 13:
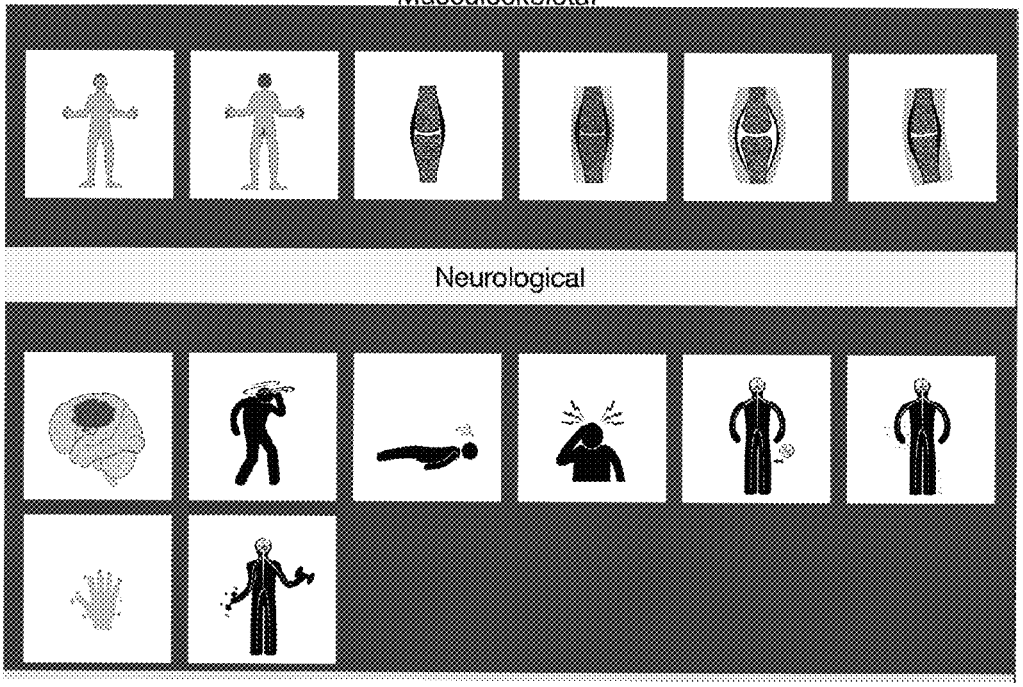
FIGS. 13 and 14 show icons that represent tasks to be completed for specific specialty examinations.
Figure 14:
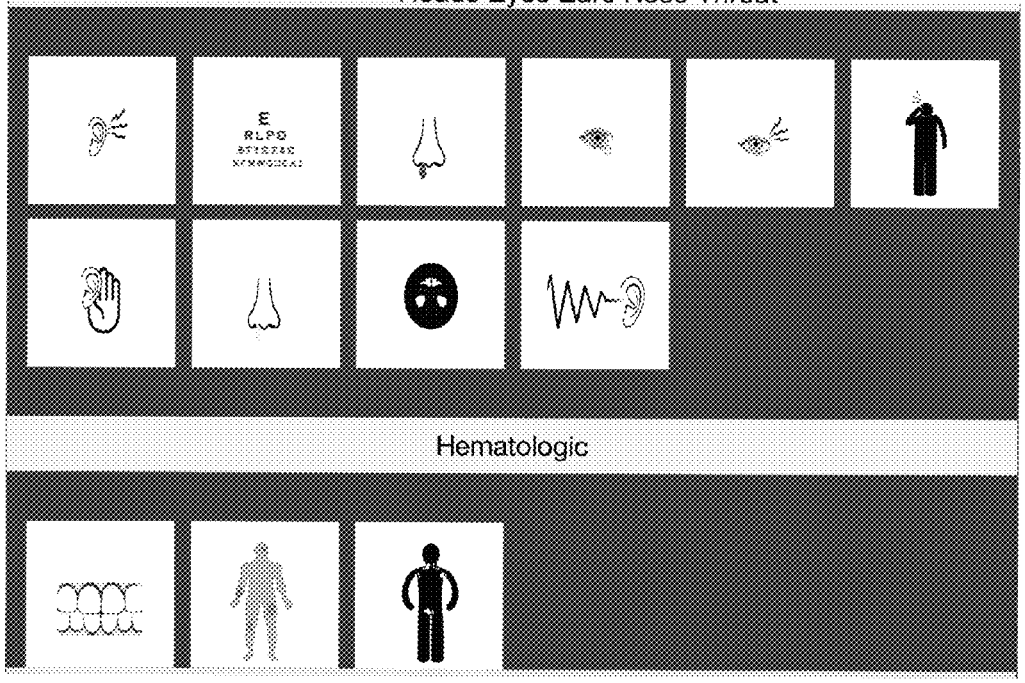

FIGS. 13 and 14 show icons that represent tasks to be completed for specific specialty examinations. FIG. 13 shows icons that indicate tasks to perform as part of a musculoskeletal examination and neurological examination. FIG. 14 shows icons that indicate tasks to perform in a "heads eyes ears nose throat" examination and hematologic examination.

Figure 15:
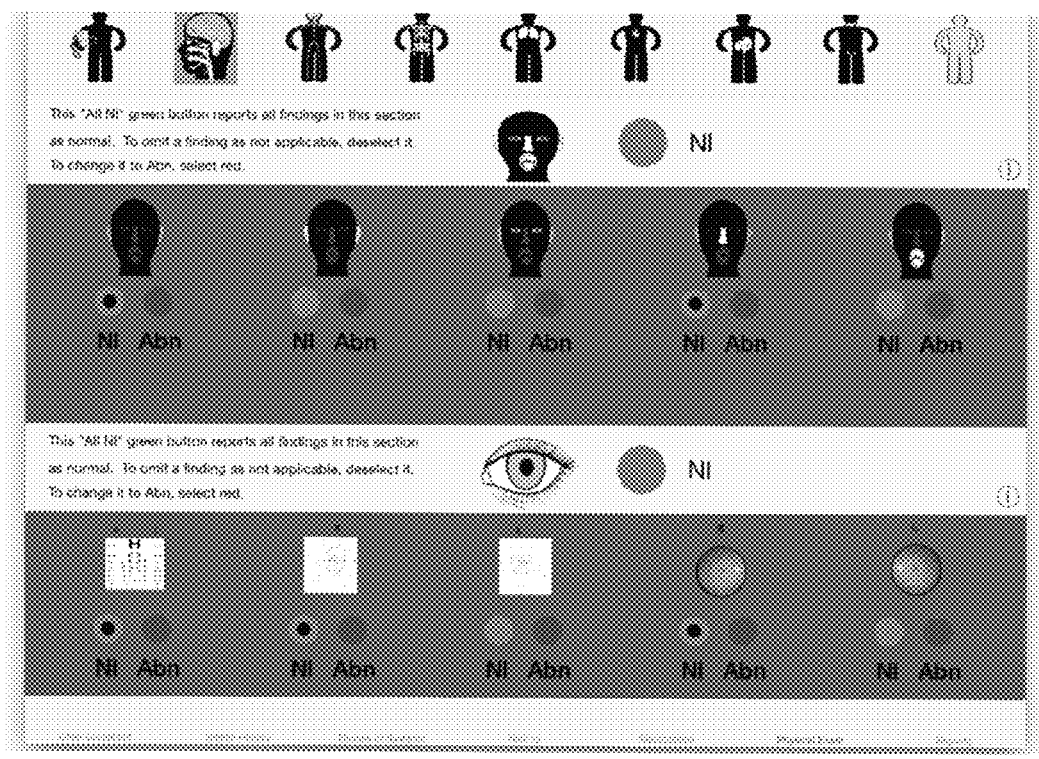
FIG. 15 shows a diagram of a human body that may be used to select the type of examination or body part to be examined.

FIG. 15 shows a diagram of a human body that may be used to select the type of examination or body part to be examined. Different representations of the human body have a specific part prominently displayed, e.g., the lungs indicative of a pulmonary examination, the heart indicative of a cardiological examination. The user can touch each displayed body representation and obtain one or more displayed sub-segments related to the prominently displayed body part or system of the touched displayed body representation.

The top rectangular display contains the multiple representations of the body parts or systems, and a button is provided (in green, for example) to enable the user to touch the button and indicate that the body part or system is normal or that any tasks performed were normal. These body representations may be considered segments, instead of text as in other embodiments.

Considering as an example, selection of the "head ears eyes nose throat" (HEENT) segment, the next lowest rectangular display area contains five head representations of the head with visual indication of the head, ears, eyes, nose or throat, and allows the user to indicate whether the specific body part is normal/abnormal or that any tasks performed were normal/abnormal. These head displays may be considered sub-segments.

The next lowest rectangular display area provides an indication of the current body part being examined, i.e., the eyes, and a button that allows the user to indicate whether the eyes are normal/abnormal or that any tasks performed were normal/abnormal.

The lowest rectangular display area provides icons indicative of specific tasks to perform on the eyes, i.e., this represents the tasks as the lowest level in the segment/sub-segment/task hierarchy. Each task has two buttons associated with it, i.e., alongside, adjacent or next to it, with one allowing the user to indicate that the task was performed with normal results and the other that the task was performed with abnormal results. An indication of the purpose of each button is provided, with text, in color, or shape.

FIGS. 16-19 are examples of the hierarchal structure of the program, and FIG. 20 is a key to understanding the hierarchy. As shown in FIG. 16, for an examination of the wrist, the wrist is a multivalue attribute having selectable tasks that require input of an integer as a result of performance of a task, e.g., a determination of the ability of the patient's wrist to perform a right flexion, left flexion, right ulnar, right radial, right extension, left extension, left radial, left ulnar. Each of these is considered an integer in that the performance of the test may result in insertion of an integer indicative of the ability of the patient to perform the task.

As shown in FIG. 17, for an examination of the thumb, the thumb is a multivalue attribute having selectable tasks that require input of an integer as a result of performance of a task, e.g., a task related to determination of the ability of the patient's thumb to perform a right IP flexion, left IP flexion, right MP flexion and left MP flexion. Each of these is considered an integer in that the performance of the test may result in insertion of an integer indicative of the ability of the patient to perform the task.

As shown in FIG. 18, for an examination of the leg, the leg is a multivalue attribute having selectable sub-segments about a particular leg or part of the leg, e.g., the right leg, right knee, right ankle, right foot, left foot, left ankle, left knee or left leg. Each of these is considered an integer in that the performance of the test may result in insertion of an integer indicative of the ability of the patient to perform the task.

As shown in FIG. 19, for an examination of the foot, the foot is a multivalue attribute having selectable sub-segments about a particular foot, i.e., the left foot or the right foot with each of these being an attribute. Selection of an attribute, when displayed on the touch screen 14 and which detection is determined by the processor 12 monitoring tapping of the touch screen 14, will provide display of parts of the right foot or left foot, e.g., the index toe, the thumb toe, the middle toe, the small toe or the ring toe. Each of these is considered an integer in that the performance of the test may result in insertion of an integer indicative of the ability of the patient to perform the task.

Although FIG. 20 includes a Boolean indicator, none are shown in FIGS. 16-19. A Boolean indicator would be one requiring, e.g., insertion of yes or no indicating whether a condition was present, For example, for the left or right leg, a Boolean indicator may be provided to indicate the presence of a limp, or not.

Figure 21:
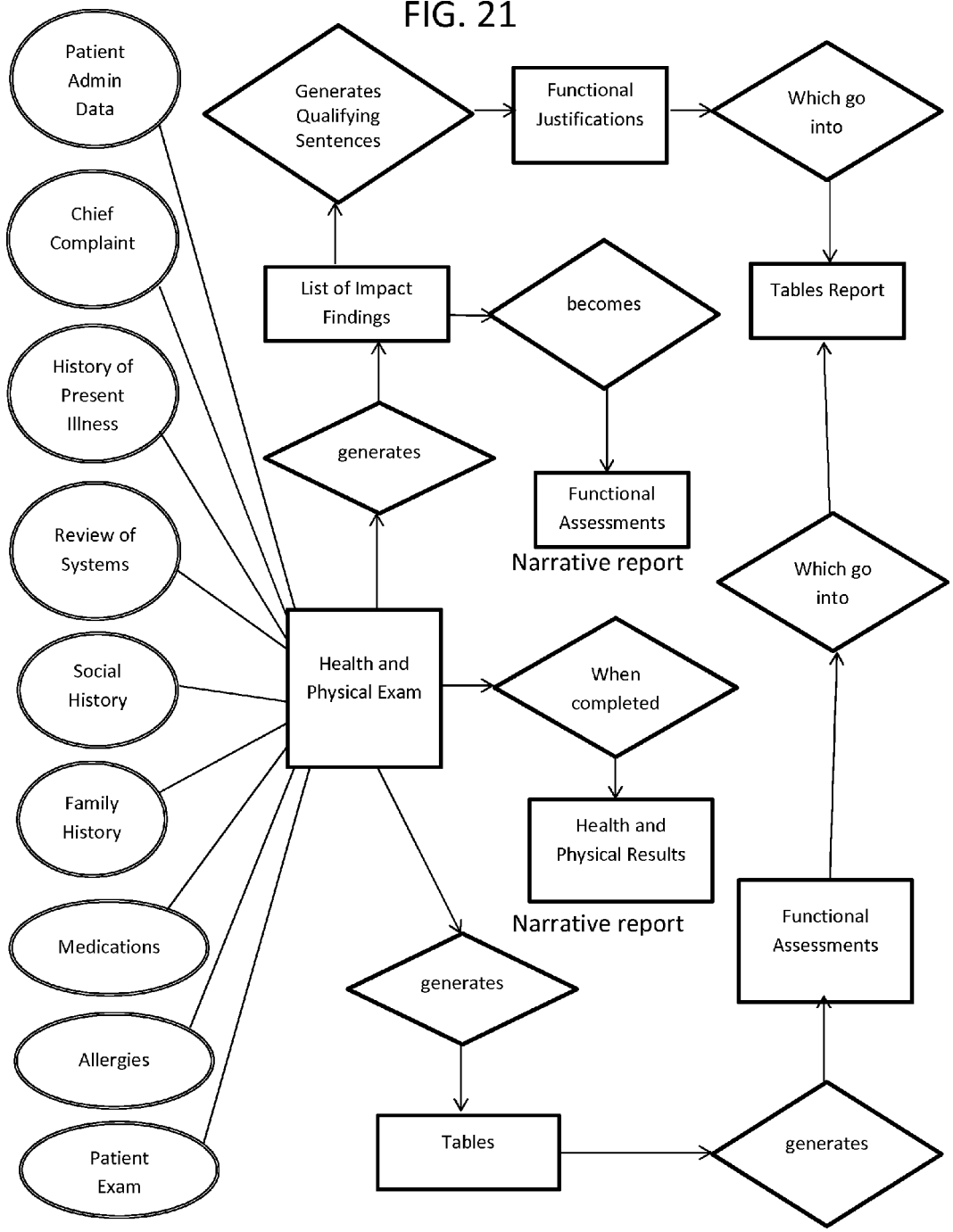
FIG. 21 is a flow chart that may be used by the program when conducting an examination.

FIG. 21 is a flow chart of one series of steps the program may execute. Initially, the program provides multivalue attributes on the touch screen 14, including patient administrative data, chief complaint, history of present illness, review of systems, social history, family history, medications, allergies and patient examination. All of these multivalue attributes may be considered segments that lead to sub-segments and tasks when conducting the health and physical examination. The data entered upon performance of the tasks generates tables which in turn generate functional assessments about the patient being examined. These functional assessment go into a tables report which in turn goes into functional justifications. The functional justifications generate qualifying sentences for inclusion into the report to be generated. Also, the list of impacting findings is generated from the data entered upon performance of the tasks (described above). The impacting findings list becomes the functional assessments for the narrative report to be generated (item 52 in FIG. 2). Also, the impacting findings list generates additional material for the physical examination, i.e., recommendations for additional tasks.

The invention thus differs fundamentally from Sorkey et al., described above, which relates to after-the-fact entry of data about activities performed on a patient. After-the-fact patient data manipulation as in Sorkey et al., is different than software used to enter data during a physical examination or diagnosis, as in the invention, whether in a medical context or in contexts outside medicine wherein an object is being examined. Generation of report based on the innovative data entry is thus unique to the invention.

The invention is also different than that described in Guimaraes, which relates to a method for manipulating existing, previously entered data. Data is not entered during an examination, and thus do not arise from a concurrent examination of a patient, e.g., receiving the patient's medical history from the patient, review of outside medical records, and performing a physical examination. The invention allows for creation of an electronic medical record without any preexisting medical data about a patient (or other object when used for non-medical purposes). The application thus automates manual workflows, reduces errors and omissions, and provides consistent, high quality reports as an output.

A software program in accordance with the invention therefore provides several benefits and advantages over existing examination procedures. For example, the program enables a higher quality examination without the distraction of note taking, and savings in time to conduct the examination resulting in a faster examination benefiting the patient and the examiner, and attendant cost savings. Another advantage is improved user and patient satisfaction.

In the context of this document, computer-readable media or medium could be any non-transitory means that can contain, store, communicate, propagate or transmit a program for use by or in connection with the method, system, apparatus or device. The computer-readable medium can be, but is not limited to (not an exhaustive list), electronic, magnetic, optical, electromagnetic, infrared, or semi-conductor propagation medium. The medium can also be (not an exhaustive list) an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM). The medium can also be paper or other suitable medium upon which a program is printed, as the program can be electronically captured, via for example, optical scanning of the paper or other medium, then compiled, interpreted, or otherwise processed in a suitable manner, if necessary, and then stored in a computer memory. Also, a computer program or data may be transferred to another computer-readable medium by any suitable process such as by scanning the computer-readable medium.

Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention which is limited only by the following claims.

The invention claimed is:

1. A method for generating at least one report from an examination of an object using a computer, comprising:
displaying on a screen, a user-selectable sequence of a plurality of data entry tools related to performance of a respective one of a plurality of tasks on the object that constitute the examination of the object;
accepting data entered using at least one of the displayed data entry tools relating to performance of the task on the object; then
storing the entered data in a memory component;
generating, using the processor, an interim report from the data entered using the at least one displayed data entry tool related to the performance of a first one of the tasks immediately after the first one of the tasks is performed and before an immediately following, second one of the tasks is performed; then
updating, using the processor, the interim report as each additional one of the tasks is performed to include information derived from the data accepted using the at least one displayed data entry tool related to the performance of the additional one of the tasks immediately after each additional one of the tasks, except for the last one of the tasks, is performed and before an immediately following one of the tasks is performed;
displaying, during the examination, a designated content area representing interim report on the screen;
enabling, using the processor, display of the interim report on the screen during the examination by monitoring use of a user interface to determine when the designated content area representing interim report display is activated and when it is determined by the processor that the designated content area representing interim report display is activated, displaying the interim report on the screen to thereby allow for display of a current report after each task during the performance of the tasks that constitute the examination prior to ending the examination; and then
generating a finished report from the entered data after all of the tasks that constitute the examination have been performed, the steps of generating the interim report, updating the interim report and generating the finished report each comprising automatically generating examination report content from completion of performance of each task performed prior to generation of the interim or finished report or updating of the interim report and for which data was entered using the at least one displayed data entry tool related to the performance of that task, and including the generated examination report content in the report.

2. The method of claim 1, further comprising, after accepting data entered using the at least one displayed data entry tool relating to performance of the task on the object,
monitoring use of the user interface to determine when an add data icon indicative of a desire to add data to a virtual clipboard is activated and when it is determined by the processor that the add data icon is activated, adding data associated with the display at the time the add icon data is activated to a virtual clipboard.

3. The method of claim 2, wherein the steps of generating the interim report and generating the finished report each further comprise selecting data from the clipboard for insertion into pre-existing templates obtained from the memory component.

4. The method of claim 1, further comprising indicating as a default setting for all of the tasks prior to initiating the examination, lack of data for all of the tasks, the steps of generating the interim report and generating the finished report including indicating in the interim and finished report, lack of data for any tasks included in the examination when there is no data entry or activity for the task.

5. The method of claim 1, further comprising:
recording information about performance of each task that constitutes the examination, the information including time and date of performance of the task;
generating a meta-record containing all of the accepted data and tasks performed during the examination including the recorded time and date of performance of each task; and
encrypting and archiving the meta-record in the memory component.

6. The method of claim 1, further comprising:
determining a schedule of the tasks to perform during the examination; and
controlling, using the processor, the screen to display the tasks to perform in accordance with the determined schedule of tasks.

7. The method of claim 6, further comprising importing the schedule of tasks into the computer.

8. The method of claim 1, further comprising:
monitoring use of the user interface to determine when a help icon indicative of a desire to receive a recommendation relating to the examination is activated; and
when it is determined by the processor that the help icon is activated, displaying on the screen, display content to enable the user of the user interface to receive help.

9. The method of claim 1, wherein each of the steps of generating the interim report and generating the finished report from the entered data comprises:
monitoring use of the user interface to determine whether a designated content area for generating a layman's report or a designated content area for generating a physician's report is activated;
when it is determined by the processor that the layman's report generating designated content area is activated, generating a layman's report from the stored data, the layman's report including data relating to future action by the patient derived from the data obtained as a result of the examination; and when it is determined by the processor that the physician's report generating designated content area is activated, generating a physician's report from the stored data that is different in content than the layman's report.

10. The method of claim 1, wherein the object is a human, further comprising:

associating each of a plurality of medical specialties relating to humans with a different set of tasks from among the plurality of tasks;

monitoring use of the user interface to determine whether a designated content area representing a respective one of the plurality of specialties is activated; and when it is determined by the processor that one specialty designated content area is activated, controlling display of content on the screen to guide the user to perform only the tasks associated with that specialty.

11. The method of claim 1, wherein, to obtain display of each of the data entry tools for the respective one of the plurality of tasks that constitute the examination, the method comprises:

displaying on the screen, a plurality of designated content areas each representing a respective segment; then monitoring use of a user interface to determine when one of the designated content areas representing a segment is activated and when it is determined by a processor that one of the designated content areas representing a segment is activated, changing the display on the screen to display a plurality of designated content areas each representing a respective sub-segment; then monitoring use of the user interface to determine when one of the designated content areas representing a sub-segment is activated and when it is determined by the processor that one of the designated content areas representing a sub-segment is activated, changing the display on the screen to display a plurality of designated content areas each associated with a respective task; and monitoring use of the user interface to determine when one of the designated content areas associated with a task is activated and when it is determined by the processor that one of the designated content areas associated with a task is activated, changing the display on the screen to display at least one data entry tool related to data obtained upon performance of the task.

12. The method of claim 11, wherein when it is determined by the processor that one of the designated content areas associated with a task is activated, changing the display to display instructions to enable performance of the task along with display of at least one data entry tool related to data obtained upon performance of that task, and the step displaying on the screen, instructions to enable performance of the task comprises displaying a pop-up window containing at least one of textual instructions and pictorial or graphical images about the task or instruments or tools needed to perform the task.

13. The method of claim 11, further comprising displaying two visually different buttons on the screen simultaneous with each designated content area associated with a respective task, a first button indicating performance of the task with normal results and a second button indicating performance of the task with abnormal results.

14. The method of claim 13, further comprising monitoring use of the user interface to determine when the first button is activated, and when it is determined by the processor that the first button is activated, placing in memory in association with the respective task, report text indicating that the task was performed and that all parameters were measured or assessed within normal ranges, and when it is determined by the processor that the second button is activated, placing in memory in association with the respective task, report text indicating that the task was performed and that at least one parameter was measured or assessed outside of a normal range.

15. The method of claim 13, further comprising:

monitoring use of the user interface to determine when the second button is activated; and when it is determined by the processor that the second button is activated, changing the display on the screen, and displaying on the screen, an input box into which a phrase or sentence associated with the respective task is insertable.

16. The method of claim 15, further comprising:

monitoring use of the user interface to determine when the input box is activated;

when it is determined by the processor that the input box is activated, displaying a keyboard on the screen to enable data entry of an exception report and/or editing of the phrase or sentence;

displaying on the screen, a microphone icon in response to the determination of the input box being activated; and when it is determined by the processor that the microphone icon is activated, enabling a speech-to-text dictation or a recording function to enter the exception report.

17. The method of claim 11, wherein the step of changing the display on the screen to display a plurality of designated content areas each representing a respective sub-segment comprises:

displaying on the screen, a plurality of designated content areas each representing a respective sub-segment in a first level of sub-segments;

monitoring use of the user interface to determine when one of the designated content areas representing a sub-segment in the first level of sub-segments is activated and when it is determined by a processor that one of the designated content areas representing a sub-segment in the first level of sub-segments is activated, changing the display on the screen to display a plurality of designated content areas each representing a respective sub-segment in a second level of sub-segments; and monitoring use of the user interface to determine when one of the designated content areas representing a sub-segment in the second level of sub-segments is activated and when it is determined by the processor that one of the designated content areas representing a sub-segment in the second level of sub-segments is activated, changing the display on the screen to display a plurality of designated content areas each associated with a respective task.

18. The method of claim 11, further comprising configuring a program to display on the screen, the plurality of designated content areas each representing a respective segment, to monitor use of the user interface, to change the display on the screen, to accept data entry relating to performance of the task, to store the entered data in the memory component, to update the interim report, and to generate the interim report and the finished report from the entered data.

19. The method of claim 18, wherein the screen is a touch screen and the user interface is a touch conversion unit associated with the touch screen, the computer program is further configured to display screens relating to tasks solely by tapping discrete designated content areas displayed on the touch screen, to thereby enable the report to be generated solely by use of the touch screen.

20. The method of claim 1, wherein the step of automatically generating examination report content from completion of performance of each task comprises displaying on the screen text selections associated with the task and retrieved from the memory component, and enabling, using the user interface, editing of the displayed text selections.

21. The method of claim 20, further comprising enabling, using the user interface, customization of the text selections.

22. A computer program embodied in non-transitory computer readable media, and configured to:
  generate at least one report from an examination of an object using a computer by displaying on a screen, a user-selectable sequence of a plurality of data entry tools related to performance of a respective one of a plurality of tasks that constitute the examination;
  accept data entered using at least one of the displayed data entry tools relating to performance of the task on the object;
  enable repetition of user interface use monitoring to allow for performance of a plurality of different tasks;
  store the entered data in a memory component; then
  generate an interim report from the entered data by generating examination report content from completion of performance of a first one of the tasks immediately after the first one of the tasks is performed and before an immediately following, second one of the tasks is performed;
  update the interim report as each additional one of the tasks is performed to include examination report content derived from the entered data related to the performance of the additional one of the tasks immediately after each additional one of the tasks, except for the last one of the tasks, is performed and before an immediately following one of the tasks is performed;
  display, during the examination, a designated content area on the screen representing interim report display;
  enable display of the interim report on the screen during the examination by monitoring use of the user interface to determine when the designated content area representing interim report display is activated and when it is determined by the processor that the designated content area representing interim report display is activated, displaying the interim report on the screen to thereby allow for display of a current report after each task during the performance of the tasks that constitute the examination prior to ending the examination; and then
  generate a finished report from the entered data after all of the tasks that constitute the examination have been performed,
  the computer program being configured to generate the interim report, update the interim report and generate the finished report by automatically generating examination report content from completion of performance of each task performed prior to generation of the interim or finished report or updating of the interim report and for which data was entered using the at least one displayed data entry tool related to the performance of that task, and including the generated examination report content in the report.

23. The computer program of claim 22, wherein, to obtain display of each of the data entry tools for the respective one of the plurality of tasks that constitute the examination, the computer program is configured to:
  display on the screen, a plurality of designated content areas each representing a respective segment;
  monitor use of a user interface to determine when one of the designated content areas representing a segment is activated and when it is determined that one of the designated content areas representing a segment is activated, change the display on the screen to display a plurality of designated content areas each representing a respective sub-segment; then
  monitor use of the user interface to determine when one of the designated content areas representing a sub-segment is activated and when it is determined that one of the designated content areas representing a sub-segment is activated, change the display on the screen to display a plurality of designated content areas each associated with a respective task; then
  monitor use of the user interface to determine when one of the designated content areas associated with a task is activated and when it is determined that one of the designated content areas associated with a task is activated, change the display on the screen to display at least one data entry tool related to data obtained upon performance of the task.

24. A computer, comprising:
  a processor,
  a memory component,
  a touch screen; and
  computer readable media containing the program of claim 22.

25. A method for generating at least one report from an examination of an object using a computer, comprising:
  displaying on a screen, a user-selectable sequence of a plurality of data entry tools related to performance of a respective one of a plurality of tasks on the object that constitute the examination of the object;
  accepting data entered using at least one of the displayed data entry tools relating to performance of the task on the object;
  storing the entered data in a memory component;
  generating, using the processor, an interim report from the data entered using the at least one displayed data entry tool related to the performance of a first one of the tasks immediately after the first one of the tasks is performed and before an immediately following, second one of the tasks is performed; then
  updating, using the processor, the interim report as each additional one of the tasks is performed to include information derived from the data accepted using the at least one displayed data entry tool related to the performance of the additional one of the tasks immediately after each additional one of the tasks, except for the last one of the tasks, is performed and before an immediately following one of the tasks is performed;
  displaying, during the examination, the interim report on the screen to thereby allow for display of a current report after each task during the performance of the tasks that constitute the examination; and then generating a finished report from the entered data after all of the tasks that constitute the examination have been performed, the steps of generating the interim report, updating the interim report and generating the finished report each comprising automatically generating examination report content from completion of performance of each task performed prior to generation of the interim or finished report or updating of the interim report and for which data was entered using the at least one displayed data entry tool related to the performance of that task, and including the generated examination report content in the report.

\* \* \* \* \*